United States Patent [19]

Takematsu et al.

[11] Patent Number: 4,521,242
[45] Date of Patent: Jun. 4, 1985

[54] SUBSTITUTED PHENYL CARBAMATES, HERBICIDAL COMPOSITIONS CONTAINING THE SAME AS ACTIVE INGREDIENT AND METHOD OF CONTROLLING WEEDS

[75] Inventors: Tetsuo Takematsu; Makoto Konnai, both of Utsunomiya; Takeo Hosogai; Takashi Nishida, both of Kurashiki, all of Japan

[73] Assignee: Kuraray Co., Ltd., Kurashiki, Japan

[21] Appl. No.: 404,780

[22] Filed: Aug. 3, 1982

[30] Foreign Application Priority Data

Oct. 26, 1981 [JP] Japan .................................. 56-171619

[51] Int. Cl.$^3$ .................... A01N 47/22; C07D 295/20
[52] U.S. Cl. ............................................. 71/94; 71/95; 71/88; 546/226; 546/313; 546/326; 548/531; 548/201; 544/161; 544/172; 260/239 BF
[58] Field of Search ............... 548/531, 201; 546/226; 71/88, 95, 94

[56] References Cited

U.S. PATENT DOCUMENTS

| | | | |
|---|---|---|---|
| 3,131,215 | 4/1964 | Lemin | 548/531 |
| 3,142,556 | 7/1964 | Weiss | 548/531 |
| 3,217,002 | 11/1965 | Weiss | 548/531 |
| 3,224,862 | 12/1965 | Weiss | 548/531 |
| 3,378,579 | 4/1968 | Allen et al. | 71/106 |
| 4,362,546 | 12/1982 | Nagase | 546/226 |

FOREIGN PATENT DOCUMENTS

| | | | |
|---|---|---|---|
| 648454 | 9/1962 | Canada | 548/531 |
| 648453 | 9/1962 | Canada | 548/531 |
| 2312906 | 9/1974 | Fed. Rep. of Germany . | |

OTHER PUBLICATIONS

Chemical Abstracts, vol. 74, (1971), 99630t.
Chemical Abstracts, vol. 73, (1970), 54978a.
Chemical Abstracts, vol. 97, (1982), 216,019n.

Primary Examiner—Norma S. Milestone
Attorney, Agent, or Firm—Burns, Doane, Swecker & Mathis

[57] ABSTRACT

There are provided novel substituted phenyl (thiono)-carbamates capable of effectively controlling broad-leaved annual weeds and annual weeds belonging to the families Gramineae and Cyperaceae such as wild Echinochloa species, monochoria, toothcup and umbrella plant, herbicidal compositions containing these (thiono)carbamates as active ingredient and a method of controlling weeds using these (thiono)carbamates. The (thiono)carbamates are substantially nonphytotoxic to useful crop plants such as the paddy rice plant.

9 Claims, No Drawings

SUBSTITUTED PHENYL CARBAMATES, HERBICIDAL COMPOSITIONS CONTAINING THE SAME AS ACTIVE INGREDIENT AND METHOD OF CONTROLLING WEEDS

BACKGROUND OF THE INVENTION

1. Field of the Invention

This invention relates to novel substituted phenyl carbamates and thionocarbamates [hereinafter collectively called "substituted phenyl (thiono)carbamates"] represented by the general formula (I)

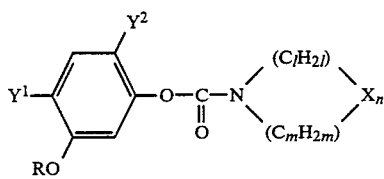

wherein X is an oxygen or sulfur atom or a vinylene group, l and m each is an integer of 1 to 4, n is an integer of 0 or 1, the heterocycle comprising the nitrogen atom, the two alkylene chains and X is 5- to 7-membered, the two alkylene chains each may be branched, $Y^1$ is a halogen atom, $Y^2$ is a hydrogen or halogen atom, R is an alkyl group, which may be interrupted by one or more oxygen atoms, or an optionally halo-substituted alkenyl or alkynyl group and Z is an oxygen or sulfur atom; herbicidal compositions containing the same as active ingredients and a method of controlling weeds using said substituted phenyl (thiono)carbamates.

2. Description of the Prior Art

It is known that certain substituted phenyl carbamates, such as 4-chlorophenyl 1-pyrrolidinecarboxylate and 2,4-dichlorophenyl 1-pyrrolidinecarboxylate, can inhibit the growth of weeds on the cultivated field in pre-emergence application and can selectively control Echinochloa species (barnyard grass, etc.) at their growth stage in the paddy filed (cf. U.S. Pat. No. 3,142,556 and Japanese Patent Application Publication No. 17,157/1971). However, these substituted phenyl carbamates are not so satisfactory in their herbicidal activity. Certain substituted phenyl thionocarbamates, such as 0-(4-chlorophenyl) 1-pyrrolidinecarbothioate and 0-(3-methoxyphenyl) 1-pyrrolidine-carbothioate, are also known to be herbicidally active against weeds on the cultivated field (cf. U.S. Pat. No. 3,217,002). However, these substituted phenyl thionocarbamates are impracticable because of their insufficient herbicidal activity and strong phytotoxicity to the desired crop plants.

SUMMARY OF THE INVENTION

An object of the invention is to provide substituted phenyl (thiono)carbamates of general formula (I) which have high herbicidal activity against a variety of weeds, herbicidal compositions containing said substituted phenyl (thiono)-carbamates as active ingredient and a method of controlling various weeds using said substituted phenyl (thiono)carbamates.

Another object of the invention is to provide substituted phenyl (thiono)carbamates of the above general formula (I) which are remarkably superior to the so far known substituted phenyl carbamates and substituted phenyl thionocarbamates especially in herbicidal activity against broad-leaved annual weeds and against annual weeds belonging to the families Gramineae and Cyperaceae.

A further object of the invention is to provide substituted phenyl (thiono)carbamates of the above general formula (I) which are almost nonphytotoxic to useful crop plants such as sunflower (*Helianthus annuus* L.), wheat (*Triticum aestivum* L.), Indian corn (*Zea Mays* L.), soybean (*Glycine Max* Merrill), peanut (*Arachis hypogaea* L.), Japanese radish (*Raphanus sativus* L.) and so on.

DETAILED DESCRIPTION OF THE INVENTION

In the above general formula (I), X is an oxygen or sulfur atom or a vinylene group, l and m each is an integer of 1 to 4 and n is an integer of 0 or 1. The heterocycle comprising the nitrogen atom, the two alkylene chains and X is 5- to 7-membered, and the two alkylene chains each may be branched. From the viewpoint of herbicidal activity, the heterocycle moiety of the substituted phenyl (thiono)carbamates of general formula (I) is preferably 5-membered or 6-membered. $Y^1$ is a halogen atom, such as a chlorine, bromine or iodine atom, and preferably is a chlorine atom. $Y^2$ is a hydrogen atom or a halogen atom, such as a chlorine, bromine or iodine atom, and preferably is a hydrogen or chlorine atom. R is an alkyl group which may be interrupted by one or more oxygen atoms, such as methyl, ethyl, propyl, butyl, pentyl, hexyl, ethoxyethyl or ethoxyethoxyethyl; an optionally halo-substituted alkenyl group, such as allyl, 2-chloroallyl, 3-chloroallyl, 2,3-dichloroallyl, 3,3-dichloroallyl, 3,3-dibromoallyl, crotyl, 3-chloro-2-methyl-2-propenyl, methallyl, prenyl, 4-chloro-3-methyl-2-butenyl or geranyl; or an optionally halo-substituted alkynyl, such as propargyl, 3-chloropropargyl, 2-butynyl, 3-butynyl or 4-chloro-3-butynyl. Z is an oxygen or sulfur atom.

It has now been found that the substituted phenyl (thiono)carbamates of the above general formula (I) have high herbicidal activity against a variety of weeds, are remarkably superior to the above-mentioned known substituted phenyl carbamates and substituted phenyl thionocarbamates especially in herbicidal activity against broad-leaved annual weeds and against annual weeds belonging to the families Gramineae and Cyperaceae and are substantially nonphytotoxic to useful crop plants such as sunflower (*Helianthus annuus* L.), wheat (*Triticum aestivum* L.), Indian corn (*Zea Mays* L.), soybean (*Glycine Max* Merrill), peanut (*Arachis hypogaea* L.), Japanese radish (*Raphanus sativus* L.) and so on.

The substituted phenyl (thiono)carbamates of general formula (I) are herbicidally active against weeds growing undesirably in such places as rice paddy fields and upland cultivated fields, for example *Elatine triandra* SCHK. (long stemmed water-wort), *Ammannia multiflora* ROXB. (red stem), *Rotala indica* KOEHNE (toothcup), *Rotala pusilla* TULASNE, *Ludwigia prostrata* ROXB. (false loosestrife), *Euphorbia supina* RAFIN (milk purslane), *Euphorbia pseudochamaesyce* FISCH. MEY. et LALLEM. (Garten-wolfsmilch), *Acelypha australis* L. (virginia copperleaf), *Fatoua villosa* NAKAI, *Chenopodium ficifolium* SMITH, *Amaranthus lividus* L. (wild amaranth), *Portulaca oleracea* L. (common purslane), *Mollugo stricta* L., *Sagina japonica* OHWI (pearlwort), *Polygonum Hydropiper* L. (water pepper), *Polygonum persicaria* L. (pink persicaria), *Polygonum lapathifolium* L. (pale-persicaria), *Polygonum*

*longisetum* DE BRUYN, *Polygonum lapathifolium* L. subsp. *nodosum* KITAM., *Polygonum aviculare* L. (knotgrass), *Polygonum nepalense* MEISN, *Deicnostema violaceum* YAMAZAKI, *Dopatrium junceum* HAMILT., *Lindernia pyxidaria* L. (false pimpernel), *Vandellia angustifolia* BENTH., *Deinstema violacea* YAMAZAKI, *Mazus japonicus* O. KUNTZE, *Mazus Miquelii* MAKINO, *Bothriospermum tenellum* FISCH. et MEY., *Trigonotis peduncularis* BENTH., *Mosla dianthera* MAXIM., *Lobelia chinensis* LOUR. (lobelia), *Erigeron annuus* PERS (annual fleabane), *Eclipta prostrata* L. (American false daisy), *Bidens tripartita* L. (erect bur marigold), *Bidens frondosa* L. (devils beggarticks), *Centipeda minima* A. BRAUN. et ASCHERS (spreading sneezeweed), *Galinsoga ciliata* BLAKE (hairy galinsoga) and other dicotyledonous weeds; *Sagittaria aginashi* MAKINO, *Alisma canaliculatum* A. BR. et BOUCHÉ, *Aneilema Keisak* HASSK, *Commelina communis* L. (Asiatic dayflower), *Eriocaulon Sieboldtianum* SIEB. et ZUCC. (pipewort), *Monochoria vaginalis* PRESL (monochoria), *Cyperus microiria* STEUD. (flat sedge), *Cyperus Iria* L. (yellowcyperus), *Lipocarpha microcephala* KUNTH, *Cyperus difformis* L. (umbrella plant), *Cyperus haspan* L., *Cyperus hakonensis* PRANCH. et SAVAT., *Cyperus sanguinolentus* VAHL, *Eleocharis pellucida* PRESL (spikerush), *Fimbristylis dichotoma* VAHL (fimbristylis), *Fimbristylis autumnalis* ROEM. et SCHULT. (autumn rush), *Scirpus juncoides* ROXB. (hardstem bulrush), *Fimbristylis miliacea* VAHL, *Cyperus serotinus* ROTTB., *Kyringa brevifolia* ROTTB. subsp. *leiolepis* T. KOYAMA (green kyllinga), *Eleocharis acicularis* ROEM. et SCHULT. (slender spikerush), *Scirpus maritimus* L. (sea clubrush), *Echinochloa Crus galli* BEAUV. typica HONDA. (watergrass), *Echinochloa oryzicola* VASING., *Echinochloa crus-galli* BEAUX. (cockspur-grass), *Beckmannia syzigachne* FERNALD (Beckmann's grass), *Digitaria adscendens* HENR. (large crab-grass), *Eleusine indica* GAERTN. (goose grass), *Setaria viridis* BEAUV. (green panicum), *Setaria glauca* BEAUV. (glaucous panicum) and other monocotyledonous weeds. The substituted phenyl (thiono)carbamates of general formula (I) produce remarkable eradicative effects against the above-mentioned weeds during the period from their germination to the two-leaf stage. Against cultivated land weeds, they are most effective at the time of germination.

Among the substituted phenyl (thiono)carbamates of general formula (I), especially preferred from the viewpoint of herbicidal activity against various weeds are compounds of the general formula (I-a)

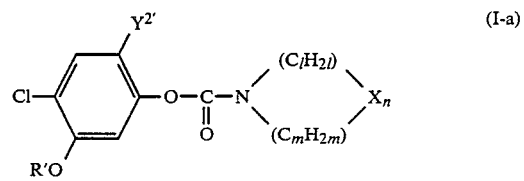

wherein X, l, m, n and z are as defined for general formula (I), and the heterocycle comprising the nitrogen atom, the two alkylene chains and X is 5- or 6-membered. $Y^{2'}$ is a hydrogen or chlorine atom and $R'$ is an alkyl group containing 1–4 carbon atoms or an optionally chloro-substituted alkenyl or alkynyl group containing 3 or 4 carbon atoms.

The following compounds, for instance, are representative of the substituted phenyl (thiono)carbamates of general formula (I):

| Compound | Structural formula | Melting point (mp) or refractive index at t° C. ($n_D^t$) |
|---|---|---|
| (1) | CH₃O– ... 4-Chloro-3-methoxyphenyl 1-pyrrolidinecarboxylate | $n_D^{27} = 1.5530$ |
| (2) | C₂H₅O– ... 4-Chloro-3-ethoxyphenyl 1-pyrrolidinecarboxylate | $n_D^{27} = 1.5442$ |
| (3) | 4-Chloro-3-isopropoxyphenyl 1-pyrrolidinecarboxylate | $n_D^{27} = 1.5350$ |
| (4) | | mp = 4 5–46.5° C. |

-continued

| Compound | Structural formula | Melting point (mp) or refractive index at t° C. ($n_D^t$) |
|---|---|---|
| | 4-Chloro-3-n-pentoxyphenyl 1-pyrrolidinecarboxylate | |
| (5) | [structure] 4-Chloro-3-(2-ethoxyethoxy)phenyl 1-pyrrolidinecarboxylate | $n_D^{27}$ = 1.5318 |
| (6) | [structure] 4-Chloro-3-[2-(2-ethoxyethoxy)ethoxy]phenyl 1-pyrrolidinecarboxylate | $n_D^{27}$ = 1.5232 |
| (7) | [structure] 3-Allyloxy-4-chlorophenyl 1-pyrrolidinecarboxylate | $n_D^{22}$ = 1.5516 |
| (8) | [structure] 4-Chloro-3-methallyloxyphenyl 1-pyrrolidinecarboxylate | $n_D^{23}$ = 1.5462 |
| (9) | [structure] 3-Crotyloxy-4-chlorophenyl 1-pyrrolidinecarboxylate | $n_D^{23}$ = 1.5499 |
| (10) | [structure] 3-(2-Chloroallyloxy)-4-chlorophenyl 1-pyrrolidine-carboxylate | mp = 68.5–73° C. |
| (11) | [structure] 4-Chloro-3-(trans-3-chloroallyloxy)phenyl 1-pyrrolidinecarboxylate | mp = 79–82.5° C. |

| Compound | Structural formula | Melting point (mp) or refractive index at t° C. ($n_D^t$) |
|---|---|---|
| (12) | 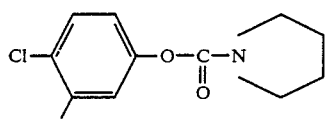 4-Chloro-3-(cis-3-chloroallyloxy)phenyl 1-pyrrolidinecarboxylate | mp = 49–54° C. |
| (13) | 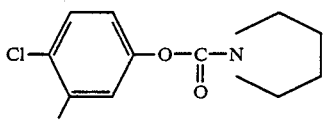 4-Chloro-3-(trans-2,3-dichloroallyloxy)phenyl 1-pyrrolidinecarboxylate | $n_D^{23} = 1.5672$ |
| (14) | 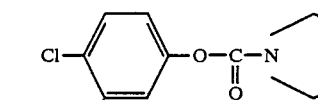 4-Chloro-3-(cis-2,3-dichloroallyloxy)phenyl 1-pyrrolidinecarboxylate | mp = 95.5–98° C. |
| (15) | 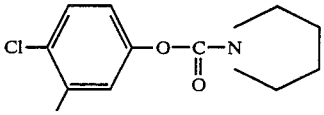 4-Chloro-3-propargyloxyphenyl 1-pyrrolidinecarboxylate | mp = 89.5–91° C. |
| (16) | 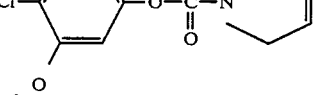 4-Chloro-3-propargyloxyphenyl 1-(3-pyrroline)carboxylate | mp = 88–91° C. |
| (17) | 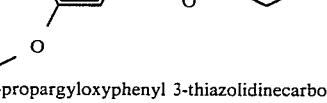 4-Chloro-3-propargyloxyphenyl 3-thiazolidinecarboxylate | mp = 71–75° C. |
| (18) | 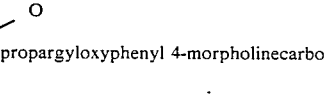 4-Chloro-3-propargyloxyphenyl 4-morpholinecarboxylate | mp = 102–105° C. |

-continued

| Compound | Structural formula | Melting point (mp) or refractive index at t° C. ($n_D^t$) |
|---|---|---|
| (19) | 4-Chloro-3-propargyloxyphenyl 1-piperidinecarboxylate | mp = 74–78° C. |
| (20) | 4-Chloro-3-propargyloxyphenyl 1-perhydroazepine-carboxylate | mp = 62–69° C. |
| (21) | 4-Chloro-3-propargyloxyphenyl 1-(2-methylpiperidine)-carboxylate | mp = 57–65° C. |
| (22) | 4,6-Dichloro-3-propargyloxyphenyl 1-pyrrolidinecarboxylate | mp = 88.5–91° C. |
| (23) | 4-Chloro-3-(3,3-dichloroallyloxy)phenyl 1-pyrrolidinecarboxylate | mp = 87–96° C. |
| (24) | 3-(3-Chloropropargyloxy)-4-chlorophenyl 1-pyrrolidinecarboxylate | mp = 47.8–50.4° C. |
| (25) | 4-Bromo-3-propargyloxyphenyl 1-pyrrolidinecarboxylate | mp = 106–108° C. |

-continued

| Compound | Structural formula | Melting point (mp) or refractive index at t° C. ($n_D^t$) |
|---|---|---|
| (26) | 4-Iodo-3-propargyloxyphenyl 1-pyrrolidinecarboxylate | mp = 123.0–125.9° C. |
| (27) | 5-Allyloxy-2,4-dichlorophenyl 1-pyrrolidinecarboxylate | mp = 77.8–78.9° C. |
| (28) | 2,4-Dichloro-5-propargyloxyphenyl 1-(3-pyrroline)-carboxylate | mp = 120.0–121.3° C. |
| (29) | 2,4-Dichloro-5-propargyloxyphenyl 3-thiazolidinecarboxylate | mp = 127.8–129.5° C. |
| (30) | 2,4-Dichloro-5-propargyloxyphenyl 4-morpholinecarboxylate | mp = 136.8–139.1° C. |
| (31) | 2,4-Dichloro-5-propargyloxyphenyl 1-piperidinecarboxylate | mp = 100.2–101.5° C. |
| (32) | O—(3-Allyloxy-4-chlorophenyl) 1-pyrrolidine-carbothioate | mp = 87.3–91.1° C. |

-continued

| Compound | Structural formula | Melting point (mp) or refractive index at t° C. ($n_D^t$) |
|---|---|---|
| (33) | 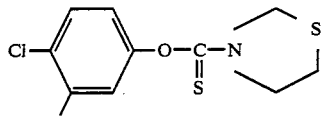<br>O—(3-Allyloxy-4-chlorophenyl) 3-thiazolidine-carbothioate | mp = 103.6–105.6° C. |
| (34) | 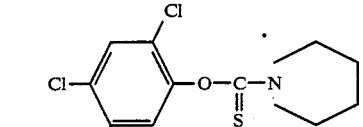<br>O—[4-Chloro-3-(3,3-dichloroallyloxy)phenyl] 1-pyrrolidinecarbothioate | mp = 112.8–116.7° C. |
| (35) | 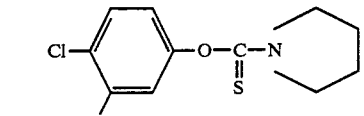<br>O—[3-(3-Chloropropargyloxy)-4-chlorophenyl] 1-pyrrolidinecarbothioate | — |
| (36) | 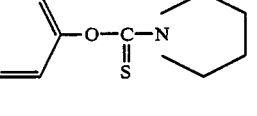<br>O—(4-Chloro-3-methoxyphenyl) 1-pyrrolidinecarbothioate | mp = 96.2–97.5° C. |
| (37) | 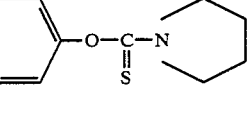<br>O—(4-Chloro-3-ethoxyphenyl) 1-pyrrolidinecarbothioate | mp = 113.3–115.7° C. |
| (38) | 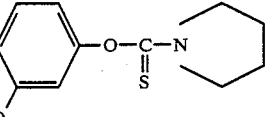<br>O—(4-Chloro-3-isopropoxyphenyl) 1-pyrrolidine-carbothioate | mp = 87.8–91.7° C. |
| (39) | 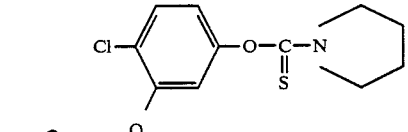<br>O—(4-Chloro-3-n-pentoxyphenyl) 1-pyrrolidine-carbothioate | mp = 68.0–69.5° C. |

| Compound | Structural formula | Melting point (mp) or refractive index at t° C. ($n_D^t$) |
|---|---|---|
| (40) | O—(3-Crotyloxy-4-chlorophenyl) 1-pyrrolidine-carbothioate | mp = 51.7–55.4° C. |
| (41) | O—(4-Chloro-3-methallyloxyphenyl) 1-pyrrolidine-carbothioate | mp = 97.0–98.5° C. |
| (42) | O—(4-Chloro-3-prenyloxyphenyl) 1-pyrrolidine-carbothioate | mp = 38.5–45.0° C. |
| (43) | O—[3-(2-Chloroallyloxy)-4-chlorophenyl] 1-pyrrolidinecarbothioate | mp = 110.8–113.7° C. |
| (44) | O—[4-Chloro-3-(trans-3-chloroallyloxy)phenyl] 1-pyrrolidinecarbothioate | mp = 97.0–99.7° C. |
| (45) | O—[4-Chloro-3-(cis-3-chloroallyloxy)phenyl] 1-pyrrolidinecarbothioate | mp = 66.3–68.0° C. |
| (46) | O—[4-Chloro-3-(2,3-dichloroallyloxy)phenyl] 1-pyrrolidinecarbothioate | Oil (room temperature) $n_D^{26} = 1.6089$ |

-continued

| Compound | Structural formula | Melting point (mp) or refractive index at t° C. ($n_D^t$) |
|---|---|---|
| (47) | O—(4-Chloro-3-propargyloxyphenyl) 1-pyrrolidine-carbothioate | mp = 103.1–104.7° C. |
| (48) | O—(3-Allyloxy-4-chlorophenyl) 4-morpholine-carbothioate | mp = 134.7–135.8° C. |
| (49) | O—(3-Allyloxy-4-chlorophenyl) 1-piperidine-carbothioate | mp = 97.8–99.0° C. |
| (50) | O—(3-Allyloxy-4-chlorophenyl) 1-(3-pyrroline)-carbothioate | mp = 102.2–105.0° C. |
| (51) | O—(3-Allyloxy-4-chlorophenyl) 1-perhydroazepine-carbothioate | Oil (room temperature) $n_D^{26}$ = 1.5842 |
| (52) | O—(3-Allyloxy-4-bromophenyl) 1-pyrrolidine-carbothioate | mp = 91.7–92.7° C. |
| (53) | O—(3-Allyloxy-4-iodophenyl) 1-pyrrolidine-carbothioate | mp = 95.3–98.4° C. |

-continued

| Compound | Structural formula | Melting point (mp) or refractive index at t° C. (n$_D^t$) |
|---|---|---|
| (54) | O—(4-Chloro-3-ethoxyethoxyphenyl) 1-pyrrolidine-carbothioate | mp = 63.3–64.6° C. |
| (55) | O—(4-Chloro-3-ethoxyethoxyethoxyphenyl) 1-pyrrolidine-carbothioate | Oil (room temperature) $n_D^{26}$ = 1.5627 |
| (56) | O—(5-Allyloxy-2,4-dichlorophenyl) 1-pyrrolidine-carbothioate | mp = 107.8–109.2° C. |
| (57) | O—(2,4-Dichloro-5-propargyloxyphenyl) 1-pyrrolidine-carbothioate | mp = 126.7–128.5° C. |
| (58) | O—(2,4-Dichloro-5-propargyloxyphenyl) 1-(3-pyrroline)carbothioate | mp = 133.6–134.9° C. |
| (59) | O—(2,4-Dichloro-5-propargyloxyphenyl) 3-thiazolidinecarbothioate | mp = 145.2–147.0° C. |

| Compound | Structural formula | Melting point (mp) or refractive index at t° C. ($n_D^t$) |
|---|---|---|
| (60) | O—(2,4-Dichloro-5-propargyloxyphenyl) 4-morpholinecarbothioate | mp = 161.0–162.3° C. |
| (61) | O—(2,4-Dichloro-5-propargyloxyphenyl) 1-piperidinecarbothioate | mp = 133.3–136.4° C. |
The substituted phneyl (thiono)carbamates of general formula (I) can easily be produced by the following methods
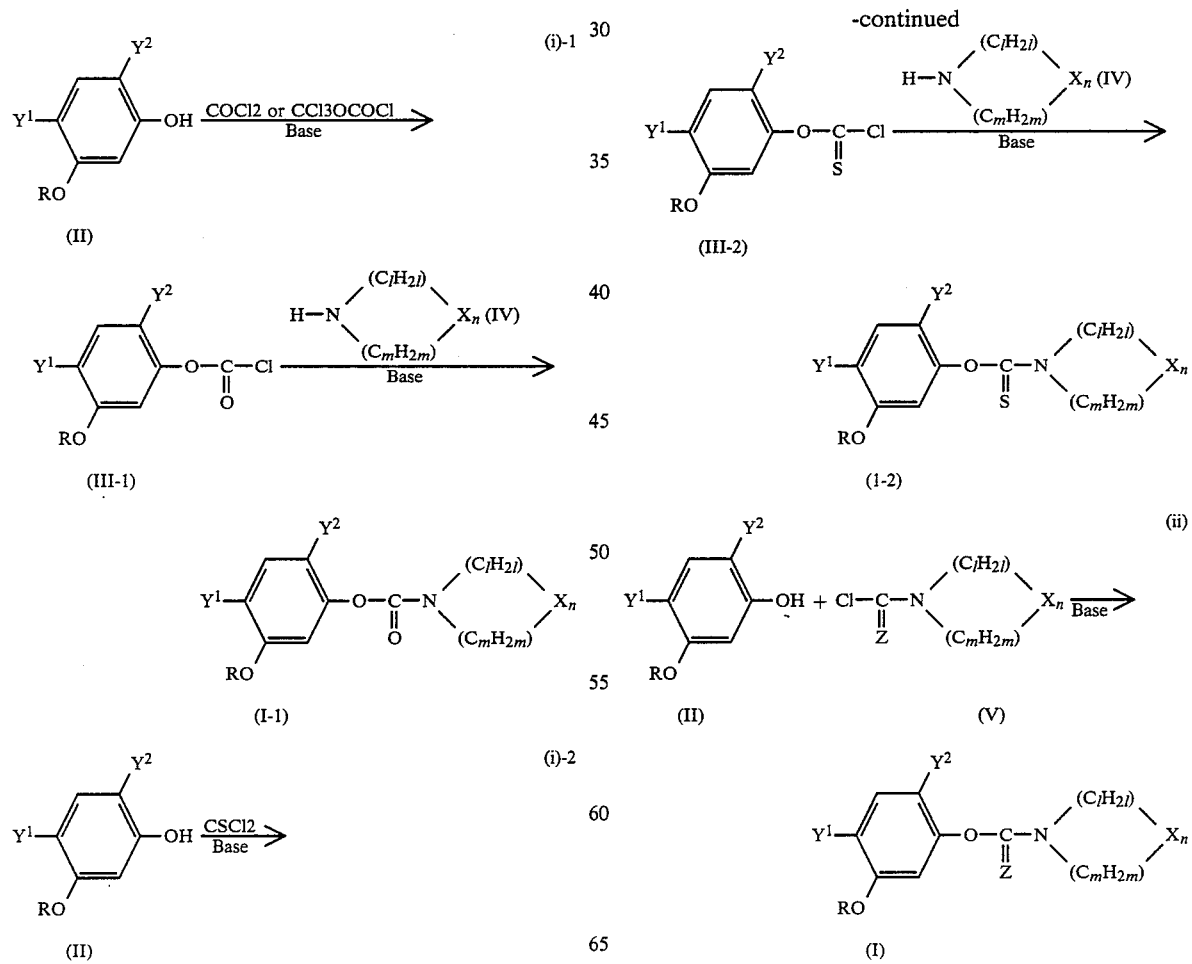

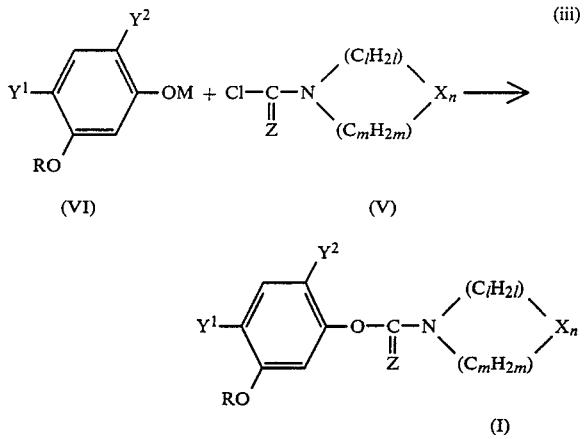

In the above formulas, X, l, m, n, $Y^1$, $Y^2$, Z and R are as defined for general formula (I), and M is an alkali metal atom.

In the carrying out method (i)-1, a compound of general formula (II) is reacted with phosgene or trichloromethyl chloroformate in the presence of a base and the resulting compound of general formula (III-1) is then reacted with a cyclic amine of general formula (IV) in the presence of a base. In carrying out method (i)-2, a compound of general formula (II) is reacted with thiophosgene in the presence of a base and the resulting compound of general formula (III-2) is then reacted with a cyclic amine of general formula (IV) in the presence of a base. In these methods, said base is, for example, an aliphatic tertiary amine (e.g. trimethylamine, triethylamine), an aromatic tertiary amine (e.g. pyridine, picoline, quinoline), a tertiary aniline (e.g. dimethylaniline, diethylaniline) or an inorganic base (e.g. sodium hydroxide, potassium hydroxide, sodium carbonate, potassium carbonate, sodium hydride, sodium amide). In each condensation reaction, the base is used in an amount of at least equivalent to the amount of the starting compound of general formula (II) or (III-1) or (III-2), preferably in an amount of 1 to 3 equivalents. In the condensation reaction between the compound of general formula (III-1) or (III-2) and the cyclic amine of general formula (IV), the latter may be used in an amount of two or more equivalents per mole of the former so that the excess amine can serve as the base. These condensation reactions are preferably carried out in a solvent. Usable solvents are, for example, such ethers as diethyl ether, tetrahydrofuran, dioxane and ethylene glycol dimethyl ether; such hydrocarbons as n-hexane and benzene; such aliphatic ketones as acetone; such chlorine-containing hydrocarbons as methylene chloride, chloroform and carbon tetrachloride; such aliphatic carboxylic acid esters as methyl acetate and ethyl acetate; dimethyl sulfoxide; and N,N-dimethylformamide. These condensation reactions are generally carried out at −50° C. to 200° C., preferably at −10° C. to 100° C.

Method (ii) shown above can be carried out under the same conditions as for method (i)-1 or (i)-2 except that the cyclic amine of general formula (IV), which is the starting material for methods (i)-1 and (i)-2, cannot be used as the base. Method (iii) is carried out by reacting the compound of general formula (VI) with the compound of general formula (V), preferably in a solvent, at a temperature of −50° C. to 200° C., preferably −10° C. to 100° C. Any of the solvents mentioned above for methods (i)-1 and (i)-2 can be used as the solvent.

In practical application, the compounds of the invention may be used alone by themselves without adding any other ingredients. For ease in use as herbicides, however, it is a general practice to formulate them with a carrier and apply the resulting formulations, if necessary after adequate dilution. In formulating, the compounds of the invention are mixed in accordance with a conventional pesticide formulation technology with a liquid or solid carrier, optionally using a surfactant, which serves as an emulsifying and/or dispersing and/or foaming agent, to give desired formulations in the form of wettable powders, emulsifiable concentrates, granular formulations, etc.

Suitable liquid carriers include, among others, aromatic hydrocarbons (e.g. xylene, toluene, benzene, alkylnaphthalene), chlorinated aromatic or aliphatic hydrocarbons (e.g. chlorobenzene, chloroethylene, methylene chloride), aliphatic or alicyclic hydrocarbons (e.g. cyclohexane, paraffin such as mineral oil fraction), alcohols (e.g. butanol, ethylene glycol and ethers or esters thereof), ketones (e.g. acetone, methyl ethyl ketone, methyl isobutyl ketone, cyclohexanone, isophorone), N,N-dimethylformamide and dimethyl sulfoxide.

Preferable solid carriers are pulverized natural minerals, such as kaolin, clay, talc, bentonite, sericite-containing kaolin (available under the trademark "Zeklite", for instance), chalk, quartz, attapulgite, montmorillonite and diatomaceous earth; and pulverized synthetic minerals, such as alumina, silicates and white carbon.

Preferable examples of the emulsifier and foaming agent are nonionic and anionic emulsifiers, such as polyoxyethylene aliphatic carboxylic acid esters, polyoxyethylene aliphatic alcohol ethers (e.g. alkylaryl polyglycol ether), alkyl-sulfonates, alkylsulfates, arylsulfonates and albumin hydrolyzate. Preferable examples of the dispersing agent are ligninsulfite waste and methylcellulose.

In preparing the herbicidal compositions of the invention, two or more of the substituted phenyl (thiono)carbamates of general formula (I) may be used combinedly so that the compositions may have excellent herbicidal activity. Furthermore, the compositions may contain fertilizers, insecticides, fungicides, other herbicides and/or plant growth regulators, which are applicable in the same field of use. In particular, it is also preferable that the substituted phenyl thionocarbamates of general formula (I-2) are applied in combination with α-(β-naphthoxy)propionic acid derivatives, such as α-(β-naphthoxy)propionanilide [hereinafter referred to as Compound (a)], N-(2-chlorophenyl)-α-(β-naphthoxy)-propionamide [Compound (b)] and N-(2-fluorophenyl)-α-(β-naphthoxy)propionamide [Compound (c)]. Such combinations can effectively control various annual and perennial weeds at low doses. In particular, the compositions can control *Cyperus serotinus* ROTTB., *Sagittaria pygmaea* MIQ. (arrowhead) and similar perennial weeds in very small doses as compared with the case in which the component herbicides each is applied alone, without producing any phytotoxic effect on useful crop plants such as paddy rice plant. The ratio of the substituted phenyl thionocarbamates of general formula (I-2) to the above-mentioned α-(β-naphthoxy)propionic acid derivative is suitably in the range of 1:0.02 to 1:50, especially desirably in the range of 1:0.1 to 1:20.

The formulated herbicidal compositions should contain at least $1 \times 10^{-3}$ percent by weight, preferably 0.01–95 percent by weight, more preferably 0.1–80 percent by weight, of the active ingredients, namely either the compounds of the invention or combinations of the compounds of the invention and other herbicidal compounds.

The compounds of the invention may be applied either in various formulation forms such as mentioned above or in application forms obtainable by further processing such formulation forms. The application forms may contain the compounds of the invention in an amount adequately selected from within a very wide range from $1 \times 10^{-5}$ to 100 percent by weight, preferably from $1 \times 10^{-3}$ to 30 percent by weight. When the compounds of the invention are used in combination with other herbicidal compounds, the total content of the active ingredients in the application forms may be selected within the same range as mentioned above, namely $1 \times 10^{-5}$ to 100 percent by weight.

The herbicidal compositions of the invention can be applied by any conventional method suited for the application form chosen. The compounds of the invention are used in an amount of at least 1 g per 10 ares, preferably 2.5 to 2,000 g per 10 ares, more preferably 10 to 1,000 g per 10 acres.

Since the herbicides of the invention are remarkably active against weeds during the period from their emergence to the two-leaf stage, they are preferably applied within this period.

The following examples of the synthesis of the compounds of the invention, formulation examples and utility examples further illustrate the invention but are by no means limitative of the invention. In the formulation examples, "part(s)" means "part(s) by weight". The compounds referred to by numbers respectively correspond to the previously mentioned substituted phenyl (thiono)carbamates (1) to (61), represented by general formula (I).

Synthesis Example 1

Synthesis of 3-allyloxy-4-chlorophenol

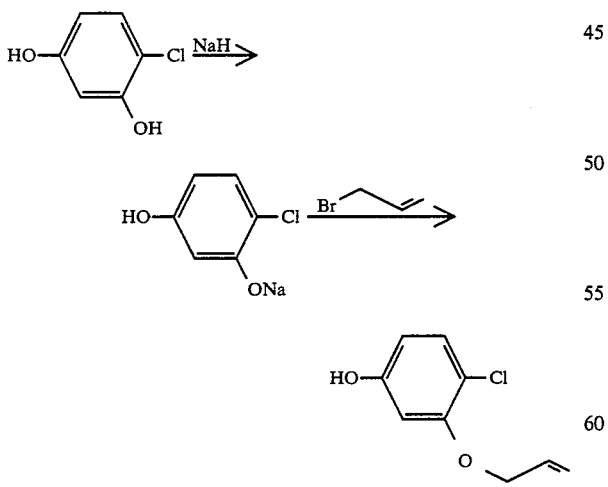

4-Chlororesorcinol (40 g) was dissolved in 500 ml of N,N-dimethylformamide. To the solution was added portionwise 13.3 g of oily sodium hydride (50% pure) to form the sodium salt of 4-chlororesorcinol. To this reaction mixture was added 33.5 g of allyl bromide, and the resulting mixture was stirred at room temperature for 18 hours, then poured into ice water and extracted with diethyl ether. The ether layer was washed with water and dried over anhydrous magnesium sulfate, and the solvent was then distilled off. Purification of the oily residue by silica gel column chromatography gave 25.6 g of 3-allyloxy-4-chlorophenol.

Synthesis of 3-allyloxy-4-chlorophenyl 1-pyrrolidine-carboxylate [Compound (7)]

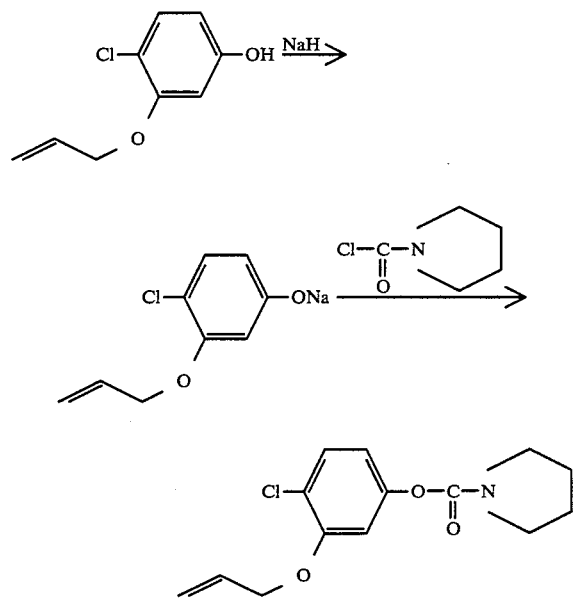

3-Allyloxy-4-chlorophenol (3.69 g) was dissolved in 40 ml of N,N-dimethylformamide and, to the solution, 0.96 g of oily sodium hydride (50% pure) was added to form the sodium salt of 3-allyloxy-4-chlorophenol. To this reaction mixture was added 3.47 g of 1-pyrrolidinecarbonyl chloride. The resulting mixture was stirred at room temperature for 18 hours, then poured into ice water and extracted with diethyl ether. The solvent was removed from the ether layer by distillation and the residue was purified by silica gel column chromatography to give 3.43 g of 3-allyloxy-4-chlorophenyl 1-pyrrolidinecarboxylate [Compound (7)]. The product had a refractive index of $n_D^{22} = 1.5516$.

Following the same procedure, there were obtained Compounds (1)–(6), (8)–(15) and (22)–(27). The melting point or refractive index of each compound was as shown hereinabove.

Synthesis Example 2

Synthesis of 4-chloro-3-propargyloxyphenyl 1-(3-pyrroline)-carboxylate [Compound (16)]

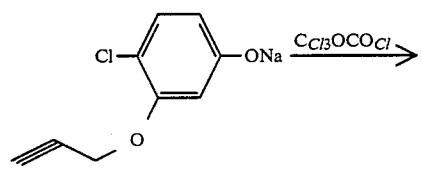

-continued

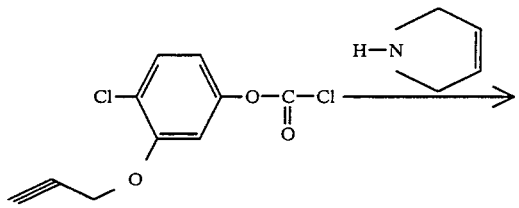

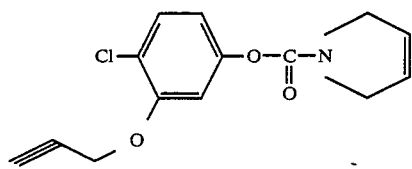

The sodium salt of 4-chloro-3-propargyloxyphenol as prepared from 14 g of 4-chloro-3-propargyloxyphenol and 28% methanol solution of sodium methylate was dissolved in 300 ml of distilled water and the solution was added dropwise to a solution of 5 ml of trichloromethyl chloroformate in 100 ml of chloroform at a temperature of 10° C. or below. The resulting reaction mixture was allowed to stand for phase separation. The chloroform layer was separated and dried over anhydrous magnesium sulfate, and the solvent was then distilled off. There was obtained 15.5 g of 4-chloro-3-propargyloxyphenyl chloroformate.

4-Chloro-3-propargyloxyphenyl chloroformate (1.00 g) was dissolved in 20 ml of diethyl ether. To the solution were added 0.34 g of 3-pyrroline and 0.43 g of triethylamine and the resulting mixture was stirred at 0° to −5° C. for 30 minutes. The reaction mixture was washed with water and the ether was distilled off from the ether layer. The thus-obtained oily substance was purified by silica gel column chromatography to give 0.51 g of 4-chloro-3-propargyloxyphenyl 1-(3-pyrroline)carboxylate[Compound (16)]. The product had a melting point of 88°–91° C.

Following the same procedure, there were obtained compounds (17)–(21) and (28)–(31). The melting point or refractive index of each compound was as shown hereinabove.

Synthesis Example 3

O-(3-Allyloxy-4-chlorophenyl) 1-pyrrolidine-carbothioate [Compound (32)]

Compound (32)

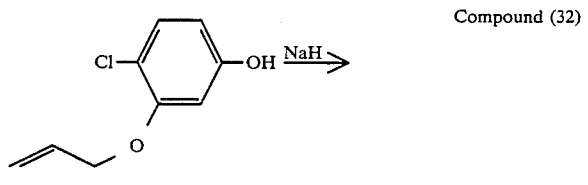

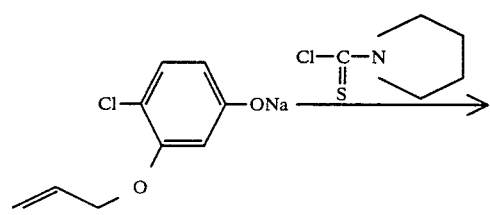

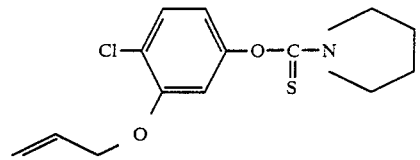

3-Allyloxy-4-chlorophenol (1.86 g) was dissolved in 20 ml of N,N-dimethylformamide. To the solution was added 0.48 g of oily sodium hydride (50% pure) to form the sodium salt of 3-allyloxy-4-chlorophenol. To this reaction mixture was added 1.94 g of 1-pyrrolidinethiocarbonyl chloride and the resulting mixture was stirred for 20 hours. Ice water was added to the reaction mixture and the organic matter was extracted with diethyl ether. The solvent was distilled off from the ether layer and the residue was purified by silica gel column chromatography to give 2.32 g of O-(3-allyloxy-4-chlorophenyl) 1-pyrrolidinecarbothioate [Compound (32)]. The product had a melting point of 87.3°–91.1° C.

Following the same procedure, there were obtained Compounds (36)–(47) and (52)–(57). The melting point or refractive index of each compound was as shown hereinabove.

Synthesis Example 4

Synthesis of O-(3-allyloxy-4-chlorophenyl) 3-thiazolidinecarbothioate [Compound (33)]

Compound (33)

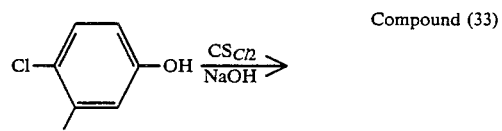

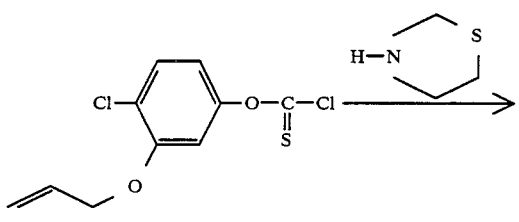

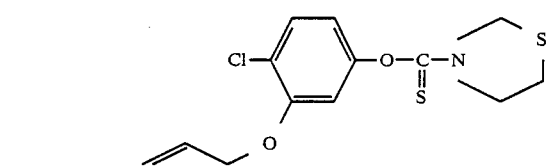

3-Allyloxy-4-chlorophenol (35.0 g) was dissolved in a solution of 7.7 g of sodium hydroxide in 30 ml of water. To the solution, there was added with stirring a solution of 14.6 ml of thiophosgene in 55.0 ml of chloroform. The reaction mixture was allowed to stand for phase separation. The chloroform layer was separated and dried over anhydrous magnesium sulfate, and the solvent was distilled off. Reduced pressure distillation of the residue gave 33.0 g of O-(3-allyloxy-4-chlorophenyl) chlorothioformate as a fraction boiling at 128°–129° C./0.4 mmHg.

O-(3-Allyloxy-4-chlorophenyl) chlorothioformate (2.63 g) was dissolved in 60 ml of diethyl ether. To this solution were added with stirring 1.01 g of thiazolidine and 1.42 ml of triethylamine. The resulting mixture was stirred for 4 hours and then washed with water. The solvent was distilled off from the ether layer. The residue was recrystallized from methanol to give 2.1 g of O-(3-allyloxy-4-chlorophenyl) 3-thiazolidinecarbothioate [Compound (33)]. The product had a melting point of 103.6°–105.6° C.

Following the same procedure, there were obtained Compounds (48)–(51) and (58)–(61). The melting point of each compound was as shown hereinbefore.

Synthesis Examples 5 and 6

Synthesis of O-[4-chloro-3-(3,3-dichloroallyloxy)-phenyl]1-pyrrolidinecarbothioate [Compound (34)] and O-[3-(3-chloropropargyloxy)-4-chlorophenyl]1-pyrrolidinecarbothioate [Compound (35)]

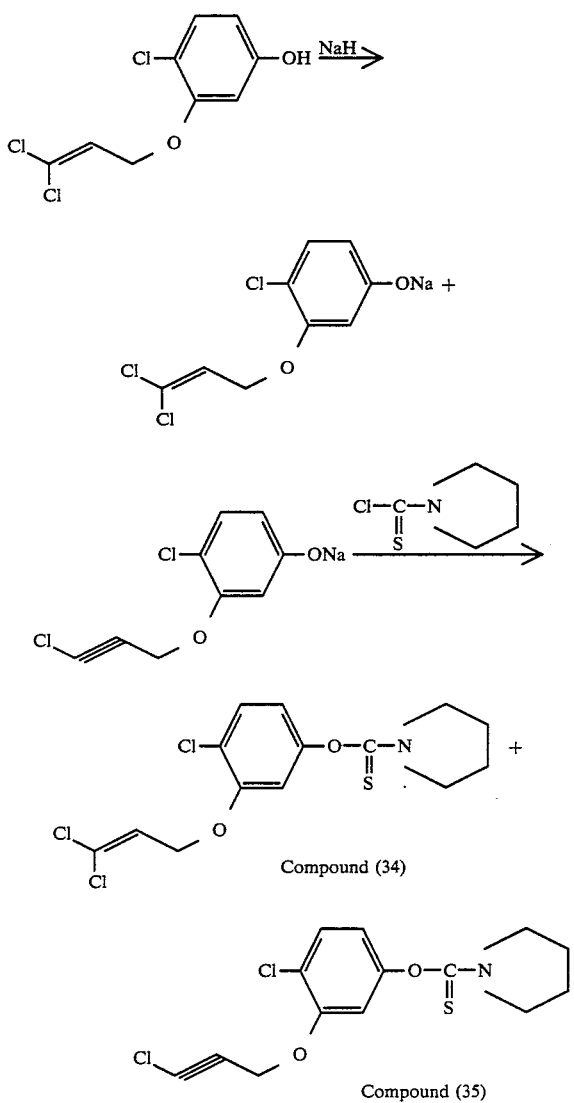

Compound (34)

Compound (35)

4-Chloro-3-(3,3-dichloroallyloxy)phenol (2.54 g) was dissolved in 20 ml of N,N-dimethylformamide. To the solution was added 0.48 g of oily sodium hydride (50% pure). To this reaction mixture was added 1.94 g of 1-pyrrolidinethiocarbonyl chloride, and the resulting mixture was stirred at room temperature for 3 hours, then poured into ice water and extracted with diethyl ether. The ether layer was washed with water and dried over anhydrous magnesium sulfate, and then the solvent was distilled off. Separation and purification of the residue by silica gel column chromatography gave 1.2 g of O-[4-chloro-3-(3,3-dichloroallyloxy)phenyl]1-pyrrolidinecarbothioate [Compound (34)] and 0.5 g of O-[3-(3-chloropropargyloxy)-4-chlorophenyl]1-pyrrolidinecarbothioate [Compound (35)]. The NMR spectral and mass spectral data for each product are shown below.

| | NMR spectrum (90 MHz)$^{CDCl_3}_{TMS}$ | Mass spectrum $[M]^+$ |
|---|---|---|
| Compound (34) | 1.80–2.30(m,4H), 3.50–4.00(m,4H), 4.65(d,J = 6Hz, 2H), 6.19(t,J = 6Hz,1H), 6.50–7.45(3H) | 365 |
| Compound (35) | 1.70–2.40(m,4H), 3.57–3.95(m,4H), 4.75(s,2H), 6.55–7.45(3H) | 329 |

Formulation Example 1

Emulsifiable concentrate

Thirty (30) parts of each of Compounds (I) to (61) was prepared, and thereto were added 60 parts of a 1:1 mixture of xylene and isophorone and 10 parts of nonionic surfactant (Sorpol 800A: a mixture of an alkylaryl ether of polyoxyethylene glycol, a polyoxyethylene sorbitan alkylate, a polyoxyethylene ester of a fatty acid and an alkylarylsulfonate, manufactured by Toho Chemical Co., Ltd.). Each mixture was stirred well to give 100 parts of an emulsifiable concentrate.

Formulation Example 2

Wettable powder

A wettable powder carrier (100 parts) was prepared by grinding and mixing 97 parts of sericite containing kaolin (Zeklite), 1.5 parts of anionic surfactant (Neoperex: sodium alkylbenzenesulfonate, manufactured by Kao-Atlas Co., Ltd.) and 1.5 parts of nonionic surfactant (Sorpol 800A as mentioned above).

Ten (10) parts of each of Compounds (1) to (61) was prepared and thereto was added 90 parts of the above wettable powder carrier. The mixture was ground and mixed to give 100 parts of a wettable powder.

Formulation Example 3

Wettable powder

Fifty (50) parts of each of Compounds (32) to (61) was prepared and mixed well with 5 parts of nonionic surfactant (Sorpol 800A as mentioned above). Further addition of 45 parts of a 1:1 mixture of talc and bentonite followed by stirring and mixing in a triturator gave 100 parts of a wettable powder.

Formulation Example 4

Granular composition

Water (10 parts) was added to 10 parts of each of Compounds (1) to (31), 80 parts of a 1:3 diluent mixture of talc and bentonite, 5 parts of white carbon and 5 parts of nonionic surfactant (Sorpol 800A as mentioned above). The mixture was kneaded, the resulting paste was extruded through sieve meshes 0.7 mm in diameter, and the extrudate was dried and cut to 0.5 to 1 mm long pieces to give 100 parts of a granular composition.

Formulation Example 5

Granular composition

Water (10 parts) was added to 10 parts of each of Compounds (32) to (61), 80 parts of a 1:3 diluent mixture of talc and bentonite, 5 parts of white carbon and 5 parts of nonionic surfactant (Sorpol 800A as mentioned above). The mixture was kneaded, the resulting paste was extruded through sieve meshes 0.7 mm in diameter, and the extrudate was dried and cut to 1 to 2 mm long pieces to give a 10% granular composition of each compound.

Using 5 parts of each of Compounds (32) to (61) and 85 parts of the diluent mixture and following the above procedure, a 5% granular composition of each compound was prepared.

Formulation Example 6

Emulsifiable concentrate

Fifteen (15) parts of each of Compounds (32) to (61) was prepared and thereto were added 15 parts of Compound (a), 60 parts of a 1:1 mixture of xylene and isophorone and 10 parts of nonionic surfactant (Sorpol 800A as mentioned above). Adequate stirring and mixing gave 100 parts of an emulsifiable concentrate.

Formulation Example 7

Wettable powder

Twenty (20) parts of each of Compounds (32) to (61) was prepared and thereto were added 20 parts of Compound (b), 20 parts of white carbon, 5 parts of sodium ligninsulfonate, 2 parts of sodium dodecylbenzenesulfonate and 33 parts of diatomaceous earth. Adequate grinding and mixing gave 100 parts of a wettable powder.

Formulation Example 8

Granular composition

Four (4) parts of each of Compounds (32) to (61) was prepared and thereto were added 6 parts of Compound (a), 80 parts of a 1:3 diluent mixture of talc and bentonite, 5 parts of white carbon and 5 parts of nonionic surfactant (Sorpol 800A as mentioned above). After mixing, 10 parts of water was added, the resulting paste was extruded through sieve meshes 0.7 mm in diameter, and the extrudate was dried and cut to 1 to 2 mm long pieces to give 100 parts of a granular composition.

Utility Example 1

Submerged soil treatment

Sieved paddy field soil was placed in a porcelain pot 9 cm in diameter, water was added, and the soil was plowed and sowed with barnyard grass (*Echinochloa crus-galli*), monochoria (*Monochoria vaginalis*), toothcup (*Rotala indica*), umbrella plant (*Cyperus difformis*) and hardstem bulrush (*Scirpus juncoides*). The pot was filled with water to the height of 2 cm over the soil surface. A wettable powder containing the test compound was prepared by the procedure of Formulation Example 2 and diluted with water to a prescribed concentration and the resulting preparation was applied onto the water surface one day after the sowing of the above weeds. The herbicidal effect on the weeds was evaluated 15 days after the application according to the criteria shown below. The results obtained are summarized below in Table 1.

Criteria for evaluation of herbicidal effects:

Inhibition of growth of weeds or withering of weeds as compared with the untreated control 5: 80% to 100%
4: Not less than 60% but less than 80%
3: Not less than 40% but less than 60%
2: Not less than 20% but less than 40%
1: Less than 20%
0: 0%

TABLE 1

| Test compound | Amount of compound (g/10a) | Barnyard grass | Monochoria | Toothcup | Umbrella plant | Hardstem bulrush |
|---|---|---|---|---|---|---|
| (1) | 25 | 4 | 5 | 5 | 5 | 2 |
|  | 50 | 5 | 5 | 5 | 5 | 3 |
|  | 100 | 5 | 5 | 5 | 5 | 4 |
|  | 250 | 5 | 5 | 5 | 5 | 5 |
| (2) | 25 | 4 | 5 | 5 | 5 | 2 |
|  | 50 | 5 | 5 | 5 | 5 | 3.5 |
|  | 100 | 5 | 5 | 5 | 5 | 4 |
|  | 250 | 5 | 5 | 5 | 5 | 5 |
| (3) | 25 | 4.5 | 5 | 5 | 5 | 3 |
|  | 50 | 5 | 5 | 5 | 5 | 4 |
|  | 100 | 5 | 5 | 5 | 5 | 4.5 |
|  | 250 | 5 | 5 | 5 | 5 | 5 |
| (4) | 25 | 4.5 | 5 | 5 | 5 | 1 |
|  | 50 | 5 | 5 | 5 | 5 | 2 |
|  | 100 | 5 | 5 | 5 | 5 | 2.5 |
|  | 250 | 5 | 5 | 5 | 5 | 3 |
| (5) | 25 | 3 | 5 | 5 | 5 | 2 |
|  | 50 | 4 | 5 | 5 | 5 | 3 |
|  | 100 | 5 | 5 | 5 | 5 | 5 |
|  | 250 | 5 | 5 | 5 | 5 | 5 |
| (6) | 25 | 2 | 4 | 4.5 | 4.5 | 1 |
|  | 50 | 4.5 | 5 | 5 | 5 | 3 |
|  | 100 | 5 | 5 | 5 | 5 | 4.5 |
|  | 250 | 5 | 5 | 5 | 5 | 5 |
| (7) | 25 | 5 | 5 | 5 | 5 | 4.5 |
|  | 50 | 5 | 5 | 5 | 5 | 5 |
|  | 100 | 5 | 5 | 5 | 5 | 5 |
|  | 250 | 5 | 5 | 5 | 5 | 5 |
| (8) | 25 | 3 | 5 | 5 | 5 | 1.5 |
|  | 50 | 5 | 5 | 5 | 5 | 3 |
|  | 100 | 5 | 5 | 5 | 5 | 5 |
|  | 250 | 5 | 5 | 5 | 5 | 5 |
| (9) | 25 | 4 | 4.5 | 4.5 | 4.5 | 1 |
|  | 50 | 5 | 5 | 5 | 5 | 2 |
|  | 100 | 5 | 5 | 5 | 5 | 4 |
|  | 250 | 5 | 5 | 5 | 5 | 5 |
| (10) | 25 | 5 | 5 | 5 | 5 | 3 |
|  | 50 | 5 | 5 | 5 | 5 | 5 |
|  | 100 | 5 | 5 | 5 | 5 | 5 |
|  | 250 | 5 | 5 | 5 | 5 | 5 |
| (11) | 25 | 4 | 4.5 | 4.5 | 5 | 1 |
|  | 50 | 5 | 5 | 5 | 5 | 2 |
|  | 100 | 5 | 5 | 5 | 5 | 3 |
|  | 250 | 5 | 5 | 5 | 5 | 5 |
| (12) | 25 | 4 | 4.5 | 4.5 | 5 | 1 |
|  | 50 | 5 | 5 | 5 | 5 | 1.5 |
|  | 100 | 5 | 5 | 5 | 5 | 2 |
|  | 250 | 5 | 5 | 5 | 5 | 5 |
| (13) | 25 | 1 | 5 | 4 | 4.5 | 0.5 |
|  | 50 | 2 | 5 | 4.5 | 5 | 2 |
|  | 100 | 5 | 5 | 5 | 5 | 4 |
|  | 250 | 5 | 5 | 5 | 5 | 5 |
| (14) | 25 | 2 | 5 | 4 | 4 | 1 |
|  | 50 | 5 | 5 | 5 | 5 | 4 |
|  | 100 | 5 | 5 | 5 | 5 | 5 |
|  | 250 | 5 | 5 | 5 | 5 | 5 |
| (15) | 25 | 5 | 5 | 5 | 5 | 4 |
|  | 50 | 5 | 5 | 5 | 5 | 4.5 |
|  | 100 | 5 | 5 | 5 | 5 | 5 |
|  | 250 | 5 | 5 | 5 | 5 | 5 |

TABLE 1-continued

| Test compound | Amount of compound (g/10a) | Barnyard grass | Monochoria | Toothcup | Umbrella plant | Hardstem bulrush |
|---|---|---|---|---|---|---|
| (16) | 25 | 3 | 4 | 5 | 5 | 4 |
|  | 50 | 5 | 5 | 5 | 5 | 5 |
|  | 100 | 5 | 5 | 5 | 5 | 5 |
|  | 250 | 5 | 5 | 5 | 5 | 5 |
| (17) | 25 | 2 | 4 | 5 | 5 | 2 |
|  | 50 | 4 | 5 | 5 | 5 | 3 |
|  | 100 | 5 | 5 | 5 | 5 | 5 |
|  | 250 | 5 | 5 | 5 | 5 | 5 |
| (18) | 25 | 3 | 3.5 | 5 | 5 | 2 |
|  | 50 | 4.5 | 5 | 5 | 5 | 3.5 |
|  | 100 | 5 | 5 | 5 | 5 | 5 |
|  | 250 | 5 | 5 | 5 | 5 | 5 |
| (19) | 25 | 4.5 | 5 | 5 | 5 | 3 |
|  | 50 | 5 | 5 | 5 | 5 | 4 |
|  | 100 | 5 | 5 | 5 | 5 | 5 |
|  | 250 | 5 | 5 | 5 | 5 | 5 |
| (20) | 25 | 2 | 4.5 | 4.5 | 5 | 2 |
|  | 50 | 3.5 | 5 | 5 | 5 | 3 |
|  | 100 | 5 | 5 | 5 | 5 | 5 |
|  | 250 | 5 | 5 | 5 | 5 | 5 |
| (21) | 25 | 2 | 3 | 4 | 3.5 | 0 |
|  | 50 | 4 | 4 | 4.5 | 4 | 1 |
|  | 100 | 5 | 5 | 5 | 5 | 2 |
|  | 250 | 5 | 5 | 5 | 5 | 3.5 |
| (22) | 25 | 5 | 5 | 5 | 5 | 4 |
|  | 50 | 5 | 5 | 5 | 5 | 4.5 |
|  | 100 | 5 | 5 | 5 | 5 | 5 |
|  | 250 | 5 | 5 | 5 | 5 | 5 |
| (23) | 25 | 4 | 4.5 | 4 | 5 | 1 |
|  | 50 | 5 | 5 | 5 | 5 | 1.5 |
|  | 100 | 5 | 5 | 5 | 5 | 2.5 |
|  | 250 | 5 | 5 | 5 | 5 | 4 |
| (24) | 25 | 4 | 4 | 5 | 5 | 2 |
|  | 50 | 4.5 | 5 | 5 | 5 | 4 |
|  | 100 | 5 | 5 | 5 | 5 | 5 |
|  | 250 | 5 | 5 | 5 | 5 | 5 |
| (25) | 25 | 5 | 5 | 5 | 5 | 4 |
|  | 50 | 5 | 5 | 5 | 5 | 4.5 |
|  | 100 | 5 | 5 | 5 | 5 | 5 |
|  | 250 | 5 | 5 | 5 | 5 | 5 |
| (26) | 25 | 4 | 5 | 5 | 5 | 3 |
|  | 50 | 5 | 5 | 5 | 5 | 4 |
|  | 100 | 5 | 5 | 5 | 5 | 5 |
|  | 250 | 5 | 5 | 5 | 5 | 5 |
| (27) | 25 | 5 | 5 | 5 | 5 | 3.5 |
|  | 50 | 5 | 5 | 5 | 5 | 4.5 |
|  | 100 | 5 | 5 | 5 | 5 | 5 |
|  | 250 | 5 | 5 | 5 | 5 | 5 |
| (28) | 25 | 5 | 4 | 5 | 4.5 | 2.5 |
|  | 50 | 5 | 5 | 5 | 5 | 4 |
|  | 100 | 5 | 5 | 5 | 5 | 4.5 |
|  | 250 | 5 | 5 | 5 | 5 | 5 |
| (29) | 25 | 4 | 4 | 4 | 3 | 1 |
|  | 50 | 5 | 5 | 5 | 5 | 3 |
|  | 100 | 5 | 5 | 5 | 5 | 4.5 |
|  | 250 | 5 | 5 | 5 | 5 | 5 |
| (30) | 25 | 4.5 | 5 | 5 | 4.5 | 2 |
|  | 50 | 5 | 5 | 5 | 5 | 3 |
|  | 100 | 5 | 5 | 5 | 5 | 5 |
|  | 250 | 5 | 5 | 5 | 5 | 5 |
| (31) | 25 | 5 | 5 | 5 | 5 | 3 |
|  | 50 | 5 | 5 | 5 | 5 | 4 |
|  | 100 | 5 | 5 | 5 | 5 | 4.5 |
|  | 250 | 5 | 5 | 5 | 5 | 5 |
| Control compound (A)(*1) | 25 | 2.5 | 3 | 2 | 1 | 0 |
|  | 50 | 3 | 4 | 3 | 3 | 1 |
|  | 100 | 4 | 4.5 | 5 | 4 | 3 |
|  | 250 | 5 | 5 | 5 | 5 | 4 |
| Control compound (B)(*2) | 25 | 1 | 1 | 2 | 1 | 0 |
|  | 50 | 3 | 2 | 3 | 2 | 0.5 |
|  | 100 | 4 | 3 | 4 | 4 | 2 |
|  | 250 | 5 | 5 | 5 | 5 | 4 |
| No treatment | | 0 | 0 | 0 | 0 | 0 |

(*1) Control Compound (A) is represented by the following formula:

Cl—⟨⟩—O—C(=O)—N⟨piperidine⟩

(*2) Control Compound (B) is represented by the following formula:

Cl—⟨⟩(Cl)—O—C(=O)—N⟨piperidine⟩

Utility Example 2

Foliage treatment

Sieved cultivated field soil was placed in a porcelain pot 9 cm in diameter, sowed with Japanese radish (*Raphanus sativus* L.), sawa millet (*Panicum crus-galli* L.), large crab-grass (*Digitaria adscendens* HENR.), green gram (*Phaseolus aureus* ROXB.) and wild amaranth (*Amaranthus lividus* L.), and covered with a 1 cm thick layer of soil. Thereafter, when each Gramineae plant reached the two-leaf stage, a wettable powder containing the test compound as prepared by the procedure of Formulation Example 2 was applied to the leaf and stem at a specified dose by spraying using an additional amount of a wetting agent and 1.5 ml of water per pot. Thirteen days after the treatment, the activity of causing withering of the test plant was evaluated according to the criteria shown below. The results obtained are summarized in Table 2.

Criteria for evaluation of withering of the test plant:

| Score | % Withering as compared with the untreated control |
|---|---|
| 5 | 80% to 100% |
| 4 | Not less than 60% but less than 80% |
| 3 | Not less than 40% but less than 60% |
| 3 | Not less than 20% but less than 40% |
| 1 | Less than 20% |
| 0 | 0% |

TABLE 2

| Test Compound | Amount of compound (g/10a) | Japanese radish | Sawa millet | Large crab-grass | Green gram | Wild amaranth |
|---|---|---|---|---|---|---|
| (1) | 250 | 1.5 | 4 | 4.5 | 1.5 | 5 |
|  | 500 | 4.5 | 5 | 5 | 2 | 5 |
|  | 1000 | 5 | 5 | 5 | 5 | 5 |
| (2) | 250 | 3 | 5 | 4.5 | 1.5 | 5 |
|  | 500 | 5 | 5 | 5 | 5 | 5 |
|  | 1000 | 5 | 5 | 5 | 5 | 5 |
| (3) | 250 | 5 | 4.5 | 4.5 | 1.5 | 5 |
|  | 500 | 5 | 5 | 5 | 3.5 | 5 |
|  | 1000 | 5 | 5 | 5 | 5 | 5 |
| (4) | 250 | 0.5 | 3 | 3.5 | 1 | 4.5 |
|  | 500 | 1 | 3.5 | 4.5 | 1.5 | 5 |
|  | 1000 | 4 | 5 | 5 | 2.5 | 5 |
| (5) | 250 | 1 | 2 | 2.5 | 2.5 | 4.5 |
|  | 500 | 5 | 4.5 | 4.5 | 5 | 5 |
|  | 1000 | 5 | 5 | 5 | 5 | 5 |
| (6) | 250 | 1.5 | 3.5 | 3.5 | 5 | 4.5 |
|  | 500 | 5 | 4.5 | 4.5 | 5 | 5 |
|  | 1000 | 5 | 4.5 | 5 | 5 | 5 |
| (7) | 250 | 3 | 5 | 5 | 5 | 4.5 |

TABLE 2-continued

| Test Compound | Amount of compound (g/10a) | Withering activity | | | | |
|---|---|---|---|---|---|---|
| | | Japanese radish | Sawa millet | Large crab-grass | Green gram | Wild amaranth |
| | 500 | 4.5 | 5 | 5 | 5 | 5 |
| | 1000 | 5 | 5 | 5 | 5 | 5 |
| (15) | 250 | 5 | 5 | 5 | 5 | 5 |
| | 500 | 5 | 5 | 5 | 5 | 5 |
| | 1000 | 5 | 5 | 5 | 5 | 5 |
| (23) | 250 | 0 | 1.5 | 0.5 | 0.5 | 4 |
| | 500 | 0 | 1.5 | 1 | 1 | 4.5 |
| | 1000 | 0.5 | 3 | 2.5 | 1 | 5 |
| No treatment | 0 | 0 | 0 | 0 | 0 | 0 |

Utility Example 3

Soil Treatment

Sieved cultivated field soil was placed in porcelain pot 9 cm in diameter, sowed with wheat (*Triticum aestivum* L.) and Japanese radish (*Raphanus sativus* L.), and covered with a 1 cm thick layer of soil. The surface soil was sowed with barnyard grass (*Echinochloa crus-galli*), large crab-grass (*Digitaria adscendens* HENR.) and wild amaranth (*Amaranthus lividus* L.) with gentle mixing. Immediately thereafter, a wettable powder containing the test compound as prepared by the procedure of Formulation Example 2 was applied to the soil at a specified dose using 2 ml of water per pot. Ten days after the soil treatment, the herbicidal effect and the phytotoxicity to the crop plant were evaluated according to the criteria shown below. The results obtained are summarized in Table 3.

| Score | Inhibition of growth, or withering of plants as compared with the untreated control |
|---|---|
| 5 | 80% to 100% |
| 4 | Not less than 60% but less than 80% |
| 3 | Not less than 40% but less than 60% |
| 2 | Not less than 20% but less than 40% |
| 1 | Less than 20% |
| 0 | 0% |

TABLE 3

| Test compound | Amount of compound (g/10 a) | Phytotoxicity to crop plant | | Herbicidal effect | | |
|---|---|---|---|---|---|---|
| | | Wheat | Japanese radish | Barnyard grass | Large crab-grass | Wild amaranth |
| Compound (1) | 50 | 0 | 0 | 0 | 1.5 | 0.5 |
| | 100 | 0 | 0 | 2 | 4.5 | 4 |
| | 200 | 0 | 0 | 3.5 | 4.5 | 3 |
| | 400 | 0 | 0 | 5 | 5 | 5 |
| Compound (2) | 50 | 0 | 0 | 1 | 3 | 0.5 |
| | 100 | 0 | 0 | 3.5 | 4.5 | 4.5 |
| | 200 | 0 | 0 | 4.5 | 5 | 5 |
| | 400 | 0.5 | 1 | 5 | 5 | 5 |
| Compound (3) | 50 | 0 | 0 | 3 | 3 | 3.5 |
| | 100 | 0 | 0 | 4 | 4 | 4.5 |
| | 200 | 0 | 0 | 4.5 | 4.5 | 5 |
| | 400 | 0 | 1 | 4.5 | 5 | 5 |
| Compound (4) | 50 | 0 | 0 | 0 | 0.5 | 1 |
| | 100 | 0 | 0 | 1 | 3 | 1 |
| | 200 | 0 | 0 | 1 | 4 | 2 |
| | 400 | 0 | 0.5 | 3 | 4 | 4.5 |
| Compound (5) | 50 | 0 | 0 | 1 | 3.5 | 0 |
| | 100 | 0 | 0 | 2 | 4 | 0 |
| | 200 | 0 | 0 | 3.5 | 4 | 3.5 |
| | 400 | 0 | 0 | 4 | 5 | 5 |
| Compound (6) | 50 | 0 | 0 | 0 | 3.5 | 0 |
| | 100 | 0 | 0 | 0.5 | 4.5 | 0.5 |
| | 200 | 0 | 0 | 2.5 | 5 | 5 |
| | 400 | 0.5 | 2.5 | 3 | 5 | 5 |
| Compound (7) | 50 | 0 | 0 | 4.5 | 4.5 | 2 |
| | 100 | 0 | 0 | 5 | 5 | 5 |
| | 200 | 0 | 0.5 | 5 | 5 | 5 |
| | 400 | 0.5 | 1 | 5 | 5 | 5 |
| Compound (8) | 50 | 0 | 0 | 1 | 2.5 | 1 |
| | 100 | 0 | 0 | 3.5 | 4 | 4.5 |
| | 200 | 0.5 | 0 | 5 | 5 | 5 |
| | 400 | 1 | 0 | 5 | 5 | 5 |
| Compound (9) | 50 | 0 | 0 | 1 | 1.5 | 3 |
| | 100 | 0 | 0 | 1 | 4 | 3 |
| | 200 | 0 | 0 | 4 | 5 | 4.5 |
| | 400 | 0.5 | 0 | 5 | 5 | 5 |
| Compound (10) | 50 | 0 | 0 | 0.5 | 3.5 | 4.5 |
| | 100 | 0 | 0 | 2 | 5 | 5 |
| | 200 | 0.5 | 0 | 2.5 | 5 | 5 |
| | 400 | 1 | 0 | 5 | 5 | 5 |
| Compound (11) | 50 | 0 | 0 | 0 | 0 | 0 |
| | 100 | 0 | 0 | 0.5 | 1 | 3 |
| | 200 | 0 | 0 | 1 | 3 | 4 |
| | 400 | 0.5 | 0 | 5 | 5 | 5 |
| Compound (12) | 50 | 0 | 0 | 0 | 0 | 0 |
| | 100 | 0 | 0 | 0 | 3 | 5 |
| | 200 | 0 | 0 | 2 | 5 | 5 |
| | 400 | 0 | 0 | 5 | 5 | 5 |
| Compound (13) | 50 | 0 | 0 | 0 | 0 | 0 |
| | 100 | 0 | 0 | 0 | 0 | 0 |
| | 200 | 0 | 0 | 0 | 0 | 0 |
| | 400 | 0 | 0 | 0 | 0.5 | 3.5 |
| Compound (14) | 50 | 0 | 0 | 0 | 0 | 0.5 |
| | 100 | 0 | 0 | 0 | 0 | 1 |
| | 200 | 0 | 0 | 0.5 | 2 | 4.5 |
| | 400 | 0 | 0 | 1.5 | 4.5 | 5 |
| Compound (15) | 50 | 0 | 0 | 5 | 5 | 5 |
| | 100 | 0 | 0 | 5 | 5 | 5 |
| | 200 | 0.5 | 0 | 5 | 5 | 5 |
| | 400 | 1.5 | 0 | 5 | 5 | 5 |
| Compound (16) | 50 | 0 | 0 | 5 | 5 | 5 |
| | 100 | 0 | 0 | 5 | 5 | 5 |
| | 200 | 1 | 0 | 5 | 5 | 5 |
| | 400 | 2 | 0.5 | 5 | 5 | 5 |
| Compound (17) | 50 | 0 | 0 | 5 | 5 | 5 |
| | 100 | 0 | 0 | 5 | 5 | 5 |
| | 200 | 0 | 0 | 5 | 5 | 5 |
| | 400 | 0 | 0 | 5 | 5 | 5 |
| Compound (18) | 50 | 0 | 0 | 5 | 5 | 5 |
| | 100 | 0 | 0 | 5 | 5 | 5 |
| | 200 | 0 | 0 | 5 | 5 | 5 |
| | 400 | 0 | 0 | 5 | 5 | 5 |
| Compound (19) | 50 | 0 | 0 | 3 | 4 | 5 |
| | 100 | 0 | 0 | 4 | 5 | 5 |
| | 200 | 0 | 0 | 5 | 5 | 5 |
| | 400 | 0 | 0 | 5 | 5 | 5 |
| Compound (20) | 50 | 0 | 0 | 1 | 2 | 4 |
| | 100 | 0 | 0 | 3 | 4 | 5 |
| | 200 | 0 | 0 | 5 | 5 | 5 |
| | 400 | 0 | 0 | 5 | 5 | 5 |
| Compound (21) | 50 | 0 | 0 | 0 | 1 | 1 |
| | 100 | 0 | 0 | 1 | 2 | 3 |
| | 200 | 0 | 0 | 3 | 4 | 5 |
| | 400 | 0 | 0 | 5 | 5 | 5 |
| Compound (22) | 50 | 0 | 0 | 5 | 5 | 5 |
| | 100 | 0 | 0 | 5 | 5 | 5 |
| | 200 | 0 | 0 | 5 | 5 | 5 |
| | 400 | 0 | 0 | 5 | 5 | 5 |
| Compound (23) | 50 | 0 | 0 | 0 | 1 | 2 |
| | 100 | 0 | 0 | 2 | 3 | 3 |
| | 200 | 0 | 0 | 3 | 4 | 5 |
| | 400 | 0 | 0 | 5 | 5 | 5 |
| Control compound (commercial product) MK-616 (*3) | 50 | 0.5 | 0 | 3.5 | 5 | 5 |
| | 100 | 2.5 | 0.5 | 4.5 | 5 | 5 |
| | 200 | 3 | 2 | 5 | 5 | 5 |
| | 400 | 4 | 3.5 | 5 | 5 | 5 |
| No | 0 | 0 | 0 | 0 | 0 | 0 |

TABLE 3-continued

| Test compound | Amount of compound (g/10 a) | Phytotoxicity to crop plant Wheat | Phytotoxicity to crop plant Japanese radish | Herbicidal effect Barnyard grass | Herbicidal effect Large crabgrass | Herbicidal effect Wild amaranth |
|---|---|---|---|---|---|---|
| treatment | | | | | | |

(*3) MK-616 is represented by the following formula

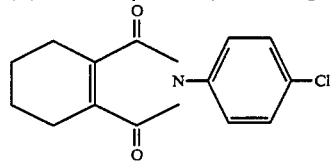

Utility Example 4
Soil treatment

Sieved cultivated field soil was placed in a porcelain pot 12 cm in diameter, sowed with Indian corn (*Zea Mays* L.), barnyard grass (*Echinochloa crus-galli*), large crab-grass (*Digitaria adscendens* HENR.), Jimsonweed (*Datura stramonium* L.) and wild amaranth (*Amaranthus lividus* L.), and covered with a 1 cm thick layer of soil. Immediately thereafter, the soil in the pot was treated with an emulsifiable concentrate of the test compound as prepared by the procedure of Formulation Example 1 using 200 liters of water per 10 ares. Fourteen days after the treatment, the herbicidal effect and the phytotoxicity to the crop plant were evaluated according to the criteria mentioned in Utility Example 3. The results obtained are summarized in Table 4.

TABLE 4

| Test compound | Amount of compound (g/10 a) | Phytotoxicity to crop plant Indian corn | Herbicidal effect Barnyard grass | Herbicidal effect Large crabgrass | Herbicidal effect Jimson weed | Herbicidal effect Wild amaranth |
|---|---|---|---|---|---|---|
| Compound (15) | 50 | 0 | 4 | 4.5 | 1 | 5 |
| | 100 | 0 | 5 | 5 | 5 | 5 |
| | 200 | 0 | 5 | 5 | 5 | 5 |
| | 400 | 0 | 5 | 5 | 5 | 5 |
| Compound (16) | 50 | 0 | 4.5 | 5 | 2 | 5 |
| | 100 | 0 | 5 | 5 | 5 | 5 |
| | 200 | 0 | 5 | 5 | 5 | 5 |
| | 400 | 0 | 5 | 5 | 5 | 5 |
| Compound (17) | 50 | 0 | 4 | 5 | 2 | 5 |
| | 100 | 0 | 5 | 5 | 4 | 5 |
| | 200 | 0 | 5 | 5 | 5 | 5 |
| | 400 | 0 | 5 | 5 | 5 | 5 |
| Compound (18) | 50 | 0 | 3 | 4 | 1 | 4 |
| | 100 | 0 | 5 | 5 | 3 | 5 |
| | 200 | 0 | 5 | 5 | 5 | 5 |
| | 400 | 0 | 5 | 5 | 5 | 5 |
| Compound (19) | 50 | 0 | 2 | 3 | 0.5 | 3 |
| | 100 | 0 | 4 | 5 | 2 | 4 |
| | 200 | 0 | 5 | 5 | 4 | 5 |
| | 400 | 0 | 5 | 5 | 5 | 5 |
| Compound (20) | 50 | 0 | 1 | 2 | 0 | 1 |
| | 100 | 0 | 3 | 4 | 1 | 3 |
| | 200 | 0 | 4 | 5 | 3 | 4 |
| | 400 | 0 | 5 | 5 | 4 | 5 |
| Compound (22) | 50 | 0 | 4 | 5 | 2 | 5 |
| | 100 | 0 | 5 | 5 | 5 | 5 |
| | 200 | 0 | 5 | 5 | 5 | 5 |
| | 400 | 0 | 5 | 5 | 5 | 5 |
| Compound (27) | 50 | 0 | 4 | 5 | 1 | 5 |
| | 100 | 0 | 5 | 5 | 2 | 5 |
| | 200 | 0 | 5 | 5 | 4 | 5 |
| | 400 | 0 | 5 | 5 | 5 | 5 |
| Compound (28) | 50 | 0 | 2 | 3 | 0 | 4 |
| | 100 | 0 | 4 | 5 | 1 | 5 |
| | 200 | 0 | 5 | 5 | 3 | 5 |
| | 400 | 0 | 5 | 5 | 5 | 5 |

TABLE 4-continued

| Test compound | Amount of compound (g/10 a) | Phytotoxicity to crop plant Indian corn | Herbicidal effect Barnyard grass | Herbicidal effect Large crabgrass | Herbicidal effect Jimson weed | Herbicidal effect Wild amaranth |
|---|---|---|---|---|---|---|
| Control compound (Commercial product) Atrazine (*4) | 50 | 0 | 2 | 2 | 1 | 5 |
| | 100 | 0 | 2.5 | 4.5 | 3 | 5 |
| | 200 | 0 | 3.5 | 5 | 5 | 5 |
| | 400 | 0 | 5 | 5 | 5 | 5 |
| No treatment | 0 | 0 | 0 | 0 | 0 | 0 |

(*4) Atrazine is represented by the following formula

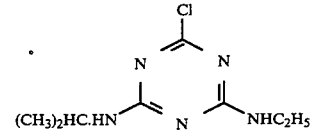

Utility Example 5
Phytotoxicity testing by soil treatment

Sieved cultivated field soil was placed in a polyethylene vat (22 cm×28 cm, 10 cm high), sowed with Japanese radish (*Raphanus sativus* L.), sunflower (*Helianthus annuus* L.), peanut (*Arachis hypogaea* L.) and soybean (*Glycine Max Merrill*), and covered with a 0.5 cm thick layer of soil. Immediately thereafter, a wettable powder containing the test compound as prepared by the procedure of Formulation Example 2 was applied to the soil at a specified dose using 200 liters of water per 10 ares. Fifteen days after the soil treatment, the phytotoxicity to the crop plants was evaluated according to the criteria mentioned in Utility Example 3. The results obtained are summarized in Table 5.

TABLE 5

| Test compound | Amount of compound (g/10a) | Phytotoxicity to crop plant Japanese radish | Phytotoxicity to crop plant Sunflower | Phytotoxicity to crop plant Peanut | Phytotoxicity to crop plant Soybean |
|---|---|---|---|---|---|
| Compound (15) | 100 | 0 | 0 | 0 | 0 |
| | 200 | 0 | 0 | 0 | 0 |
| | 400 | 0 | 0 | 0 | 0 |
| | 800 | 0 | 0.5 | 0.5 | 1 |
| Compound (16) | 100 | 0 | 0 | 0 | 0 |
| | 200 | 0 | 0 | 0 | 0 |
| | 400 | 0.5 | 0 | 0.5 | 0.5 |
| | 800 | 1 | 1 | 2 | 1 |
| Compound (17) | 100 | 0 | 0 | 0 | 0 |
| | 200 | 0 | 0 | 0 | 0 |
| | 400 | 0 | 0 | 0 | 0 |
| | 800 | 0 | 0 | 0 | 0 |
| Compound (18) | 100 | 0 | 0 | 0 | 0 |
| | 200 | 0 | 0 | 0 | 0 |
| | 400 | 0 | 0 | 0 | 0 |
| | 800 | 0 | 0 | 0 | 0 |
| Compound (19) | 100 | 0 | 0 | 0 | 0 |
| | 200 | 0 | 0 | 0 | 0 |
| | 400 | 0 | 0 | 0 | 0 |
| | 800 | 0 | 0 | 0 | 0 |
| Compound (20) | 100 | 0 | 0 | 0 | 0 |
| | 200 | 0 | 0 | 0 | 0 |
| | 400 | 0 | 0 | 0 | 0 |
| | 800 | 0 | 0 | 0 | 0 |
| Compound (21) | 100 | 0 | 0 | 0 | 0 |
| | 200 | 0 | 0 | 0 | 0 |
| | 400 | 0 | 0 | 0 | 0 |
| | 800 | 0 | 0 | 0 | 0 |
| MK-616 | 100 | 0 | 0 | 0 | 0 |
| | 200 | 1 | 0 | 0 | 0 |
| | 400 | 1.5 | 0 | 1.5 | 0.5 |
| | 800 | 4 | 0.5 | 4 | 2 |
| No | 0 | 0 | 0 | 0 | 0 |

TABLE 5-continued

| Test compound treatment | Amount of compound (g/10a) | Phytotoxicity to crop plant | | | |
|---|---|---|---|---|---|
| | | Japanese radish | Sun-flower | Peanut | Soybean |

Utility Example 6

Submerged soil treatment

Paddy field soil was placed in a pot 12 cm in diameter and sowed with barnyard grass (*Echinochloa crus-galli*), hardstem bulrush (*Scirpus juncoides*), toothcup (*Rotala indica*), monochoria (*Monochoria vaginalis*) and *Cyperus serotinus*. Furthermore, rice seedlings at the 2.5-leaf stage were transplanted. Three days later, the pot was filled with water to the height of 3 cm over the soil surface. A wettable powder containing the test compound as prepared by the procedure of Formulation Example 3 was diluted with water to a prescribed concentration and the resulting preparation was dropped onto the water surface. The herbicical effect on the weeds and injury to the paddy rice plant were evaluated 14 days after the application according to the criteria shown below. The results obtained are summarized in Table 6.

| Score | Inhibition or withering of weeds as compared with the untreated control |
|---|---|
| 5 | 80% to 100% |
| 4 | Not less than 60% but less than 80% |
| 3 | Not less than 40% but less than 60% |
| 2 | Not less than 20% but less than 40% |
| 1 | Less than 20% |
| 0 | 0% |

Criteria for evaluation of phytotoxicity to paddy rice plant:

| | Browing of leaf sheath portion of the paddy rice plant |
|---|---|
| +++ | To a very large extent |
| ++ | To a moderate extent |
| + | To a small extent |
| ± | To a slight extent |
| − | None |

TABLE 6

| Test compound | Amount of compound (g/10 a) | Herbicidal effect | | | | | Phytotoxicity to paddy rice plant |
|---|---|---|---|---|---|---|---|
| | | Barnyard grass | Hardstem bulrush | Toothcup | Monochoria | *Cyperus serotinus* | |
| Compound (41) | 12.5 | 1 | 1 | 5 | 4 | 1 | − |
| | 25 | 3 | 3 | 5 | 5 | 1 | − |
| | 50 | 4 | 4 | 5 | 5 | 4 | − |
| | 100 | 5 | 5 | 5 | 5 | 5 | ± |
| Control compound (O) (*5) | 12.5 | 0 | 0 | 1 | 1 | 0 | − |
| | 25 | 1 | 0 | 2 | 2 | 1 | − |
| | 50 | 1 | 0 | 2 | 2 | 2 | ++ |
| | 100 | 2 | 1 | 4 | 3 | 2 | +++ |
| Control compound (D) (*6) | 12.5 | 0 | 0 | 1 | 1 | 0 | − |
| | 25 | 0 | 0 | 2 | 2 | 0 | − |
| | 50 | 0 | 0 | 4 | 3 | 1 | − |
| | 100 | 0 | 0 | 5 | 5 | 2 | ± |
| Control compound (commercial product) MO | 12.5 | 0 | 0 | 2 | 1 | 1 | − |
| | 25 | 2 | 0 | 3 | 2 | 2 | − |
| | 50 | 3 | 1 | 5 | 4 | 3 | − |
| | 100 | 4 | 1 | 5 | 5 | 5 | ± |
| No treatment | 0 | 0 | 0 | 0 | 0 | 0 | − |

(*5) Control Compound (C) is represented by the following formula

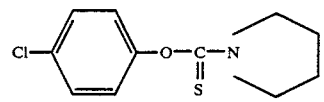

(*6) Control Compound (D) is represented by the following formula

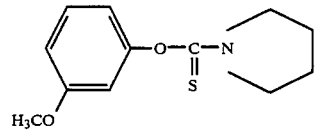

Utility Example 7

Submerged soil treatment

Paddy field soil was placed in a pot 12 cm in diameter and sowed with barnyard grass (*Echinochloa crus-galli*), hardstem bulrush (*Scirpus juncoides*), toothcup (*Rotala indica*), monochoria (*Monochoria vaginalis*) and *Cyperus serotinus*. Three days later, the pot was filled with water to the height of 3 cm over the soil surface. An emulsifiable concentrate of the test compound as prepared by the procedure of Formulation Example 1 was diluted with water to a prescribed concentration and the resulting preparation was dropped onto the water surface. The herbicidal effect was evaluated 14 days after the treatment according to the criteria mentioned in Utility Example 6. The results obtained are shown in Table 7.

TABLE 7

| Test compound | Amount of compound (g/10a) | Herbicidal effect | | | | |
|---|---|---|---|---|---|---|
| | | Barnyard grass | Hardstem bulrush | Toothcup | Monochoria | *Cyperus serotinus* |
| Compound (32) | 12.5 | 3 | 1 | 5 | 3 | 2 |
| | 25 | 4 | 3 | 5 | 4 | 2 |
| | 50 | 5 | 4 | 5 | 5 | 4 |
| | 100 | 5 | 5 | 5 | 5 | 5 |
| | 200 | 5 | 5 | 5 | 5 | 5 |
| Control compound (C) | 12.5 | 0 | 0 | 1 | 1 | 0 |
| | 25 | 1 | 0 | 2 | 2 | 1 |
| | 50 | 1 | 0 | 2 | 2 | 2 |
| | 100 | 2 | 1 | 4 | 3 | 2 |
| | 200 | 5 | 3 | 5 | 5 | 3 |
| No treatment | | 0 | 0 | 0 | 0 | 0 |

Utility Example 8

Submerged soil treatment

Paddy field soil was placed in a pot 12 cm in diameter and sowed with barnyard grass (*Echinochloa crus-galli*), hardstem bulrush (*Scirpus juncoides*) and broad-leaved weeds [toothcup (*Rotala indica*) and monochoria (*Monochoria vaginalis*)], and furthermore rice seedlings at the 2.5-leaf stage were transplanted. The pot was filled with water to the height of 2 cm over the soil surface. A wettable powder containing the test compound as prepared by the procedure of Formulation Example 3 was diluted with water to a prescribed concentration. The resulting preparation was dropped onto the water surface and, two weeks later, the herbicidal effect and the phytotoxicity to the paddy rice plant were evaluated according to the criteria mentioned in Utility Example 6. The results obtained are shown in Table 8.

Utility Example 9

Cultivated field soil treatment

Sieved cultivated field soil was placed in a polyethylene vat (20 cm × 15 cm), sowed with large crab-grass (*Digitaria adscendens* HENR.), wild amaranth (*Amaranthus lividus* L.), Japanese radish (*Raphanus sativus* L.), rape (*Brassica campestris* L.) and sunflower (*Helianthus annuus* L.), and covered with a 1 cm thick layer of soil. One day later, a wettable powder containing Compound (41) as prepared by the procedure of Formulation Example 3 was applied to the soil at a specified dose using 200 liters of water per 10 ares. Fifteen days later, the herbicidal effect was evaluated according to the criteria mentioned in Utility Example 6 and the phytotoxicity to the crop plants was also evaluated according to the criteria shown below. The results obtained are shown in Table 9. Criteria for phytotoxicity evaluation:

TABLE 8

| | Amount of compound (g/10 a) | | | | | | | | | | | |
|---|---|---|---|---|---|---|---|---|---|---|---|---|
| | 100 | | | | 50 | | | | 25 | | | |
| | Weeds and paddy rice plant | | | | | | | | | | | |
| | Barnyard grass | Broad-leaved weeds | Hardstem bulrush | Paddy rice plant | Barnyard grass | Broad-leaved weeds | Hardstem bulrush | Paddy rice plant | Barnyard grass | Broad-leaved weeds | Hardstem bulrush | Paddy rice plant |
| Compound (33) | 5 | 5 | 5 | — | 5 | 5 | 5 | — | 5 | 5 | 5 | — |
| Compound (34) | 5 | 5 | 4.5 | — | 5 | 4.5 | 4 | — | 4 | 4 | 3 | — |
| Compound (35) | 5 | 5 | 5 | — | 5 | 5 | 5 | — | 5 | 5 | 5 | — |
| Compound (36) | 5 | 5 | 5 | ± | 5 | 5 | 5 | — | 4 | 5 | 5 | — |
| Compound (37) | 5 | 5 | 5 | ± | 4.5 | 5 | 5 | ± | 3.5 | 5 | 4.5 | — |
| Compound (38) | 5 | 5 | 5 | — | 4.5 | 5 | 5 | — | 4 | 5 | 4.5 | — |
| Compound (39) | 5 | 5 | 5 | — | 5 | 5 | 4.5 | — | 4 | 4.5 | 3 | — |
| Compound (40) | 5 | 5 | 5 | — | 4.5 | 5 | 4.5 | — | 4 | 4.5 | 3.5 | — |
| Compound (42) | 4 | 5 | 3.5 | — | 3 | 4.5 | 3 | — | 3 | 4 | 3 | — |
| Compound (43) | 5 | 5 | 4.5 | — | 5 | 5 | 4 | — | 4 | 5 | 3 | — |
| Compound (44) | 5 | 5 | 5 | — | 5 | 4.5 | 4.5 | — | 4.5 | 4 | 3 | — |
| Compound (45) | 5 | 5 | 5 | — | 5 | 5 | 4.5 | — | 4 | 5 | 3 | — |
| Compound (47) | 5 | 5 | 5 | ± | 5 | 5 | 5 | ± | 5 | 5 | 5 | — |
| Compound (48) | 5 | 5 | 5 | ± | 5 | 5 | 5 | — | 4 | 5 | 4.5 | — |
| Compound (49) | 5 | 5 | 5 | — | 5 | 5 | 5 | — | 4.5 | 5 | 5 | — |
| Compound (50) | 5 | 5 | 5 | ± | 5 | 5 | 5 | — | 4.5 | 5 | 5 | — |
| Compound (51) | 5 | 5 | 5 | — | 4 | 5 | 4 | — | 3 | 5 | 3 | — |
| Compound (52) | 5 | 5 | 5 | ± | 5 | 5 | 5 | ± | 4.5 | 5 | 4 | — |
| Compound (54) | 5 | 5 | 4.5 | ± | 5 | 4.5 | 4 | ± | 4 | 4 | 3 | — |
| Compound (55) | 5 | 5 | 5 | ± | 5 | 5 | 4 | — | 4.5 | 5 | 4 | — |
| Compound (56) | 5 | 5 | 5 | ± | 5 | 5 | 5 | — | 5 | 5 | 4.5 | — |
| Compound (57) | 5 | 5 | 5 | ± | 5 | 5 | 5 | ± | 5 | 5 | 4 | — |
| Compound (58) | 5 | 5 | 4 | ± | 5 | 5 | 3 | — | 5 | 5 | 2 | — |
| Compound (59) | 5 | 5 | 4.5 | ± | 5 | 5 | 3.5 | — | 5 | 5 | 3 | — |
| Compound (60) | 5 | 5 | 4 | — | 5 | 5 | 3 | — | 3 | 4 | 2 | — |
| Compound (61) | 5 | 5 | 4 | ± | 5 | 5 | 3 | — | 4.5 | 4.5 | 2 | — |
| No treatment | 0 | 0 | 0 | — | 0 | 0 | 0 | — | 0 | 0 | 0 | — |

| Extent of phytotoxicity to crop plants | |
|---|---|
| +++ | Very large |
| ++ | Moderate |
| + | Small |
| ± | Slight |
| − | None |

TABLE 9

| Amount of compound (g/10a) | Herbicidal effect | | Phytotoxicity to the crop plant | | |
|---|---|---|---|---|---|
| | Large crab-grass | Wild amaranth | Japanese radish | Rape | Sunflower |
| 50 | 3 | 3.5 | — | — | — |
| 100 | 4.5 | 4.5 | — | — | — |
| 200 | 5 | 5 | — | ± | — |
| No treatment | 0 | 0 | — | — | — |

Utility Example 10

Outdoor vat test (treatment with wettable powder)

Paddy field soil was placed in a 800-cm² vat and sowed with barnyard grass (*Echinochloa crus-galli*), hardstem bulrush (*Scirpus juncoides*) and broad-leaved weeds [toothcup (*Rotala indica*) and monochoria (*Monochoria vaginalis*)]. Furthermore, tubers of arrowhead (*Sagittaria pygmaea*) were embedded in the soil. The vat was filled with water to the height of 3 cm over the soil surface and an aqueous dilution of a prescribed amount of a wettable powder containing Compound (32), Compound (41) or MO was applied to the water surface. Fifteen days later, the herbicidal effect was evaluated according to the criteria described in Utility Example 6. The results obtained are shown in Table 10.

TABLE 10

| Test compound | Amount of compound (g/10a) | Herbicidal effect | | | |
|---|---|---|---|---|---|
| | | Barn-yard grass | Hard-stem bulrush | Broad-leaved weeds | Arrow-head |
| Compound (32) | 25 | 4 | 3 | 5 | — |
| | 50 | 4.5 | 4 | 5 | — |
| | 100 | 5 | 5 | 5 | 4.5 |
| | 200 | 5 | 5 | 5 | 5 |
| Compound (41) | 25 | 3 | 3 | 5 | — |
| | 50 | 5 | 4 | 5 | — |
| | 100 | 5 | 5 | 5 | 3.5 |
| | 200 | 5 | 5 | 5 | 4 |
| Control compound (Commercial product) MO | 50 | 3 | 1 | 3 | — |
| | 100 | 4 | 3 | 5 | 0 |
| | 200 | 5 | 4 | 5 | 2 |
| No | — | 0 | 0 | 0 | 0 |

TABLE 10-continued

| Test compound treatment | Amount of compound (g/10a) | Herbicidal effect | | | |
|---|---|---|---|---|---|
| | | Barn-yard grass | Hard-stem bulrush | Broad-leaved weeds | Arrow-head |

Utility Example 11

Outdoor vat test (treatment with granular composition)

Paddy field soil was placed in a 675-cm² vat and sowed with barnyard grass (*Echinochloa crus-galli*), hardstem bulrush (*Scirpus juncoides*), broad-leaved weeds [toothcup (*Rotala indica*) and monochoria (*Monochoria vaginalis*)] and umbrella plant (*Cyperus difformis*). Furthermore, tubers of arrowhead (*Sagittaria pygmaea*) were embedded in the soil. After the vat was filled with water to the height of 2 cm over the soil surface, a 5% granular composition containing Compound (32) or (41) as prepared by the procedure of Formulation Example 5 was applied to the water surface. Twenty days later, the herbicidal effect was evaluated according to the criteria described in Utility Example 6. The results obtained are shown in Table 11.

TABLE 11

| Test compound | Amount of 5% granular composition (kg/10a) | Herbicidal effect | | | | |
|---|---|---|---|---|---|---|
| | | Barnyard grass | Hardstem bulrush | Broad-leaved weeds | Umbrella plant | Arrowhead |
| Compound (32) | 0.5 | 5 | 3.5 | 5 | 5 | 4.5 |
| | 1 | 5 | 4.5 | 5 | 5 | 5 |
| | 2 | 5 | 5 | 5 | 5 | 5 |
| | 3 | 5 | 5 | 5 | 5 | 5 |
| Compound (41) | 0.5 | 4 | 3 | 5 | 4.5 | 4 |
| | 1 | 5 | 3.5 | 5 | 5 | 4 |
| | 2 | 5 | 4 | 5 | 5 | 4.5 |
| | 3 | 5 | 5 | 5 | 5 | 5 |
| No treatment | — | 0 | 0 | 0 | 0 | 0 |

Utility Example 12

Submerged soil treatment

Sieved paddy field soil was placed in a porcelain pot 12 cm in diameter and, after addition of water, plowed and sowed with barnyard grass (*Echinochloa crus-galli*), monochoria (*Monochoria vaginalis*), toothcup (*Rotala indica*), umbrella plant (*Cyperus difformis*) and hardstem bulrush (*Scirpus juncoides*). Furthermore tubers of *Cyperus serotinus* and arrowhead (*Sagittaria pygmaea*) were transplanted after forced sprouting. Then two rice seedlings (*Oryza sativa* L, Nipponbare strain) at the two-leaf stage were transplanted in a bundle and the pot was filled with water to the height of 2 cm over the soil surface. A wettable powder containing the test compound, which was prepared by the procedure of Formulation Example 2, was diluted with water to a prescribed concentration and the resulting preparation was applied onto the water surface three days after the transplantation of the rice seedlings. The herbicidal effect on the weeds and injury to the paddy rice plant (inhibition of growth of the paddy rice plant) were evaluated 20 days after the application according to the criteria shown below. The results obtained are shown in Table 12 and Table 13. Criteria for evaluation of herbicidal effect:

| Score | Inhibition or withering of weeds as compared with the untreated control |
|---|---|
| 5 | 80% to 100% |
| 4 | Not less than 60% but less than 80% |
| 3 | Not less than 40% but less than 60% |
| 2 | Not less than 20% but less than 40% |
| 1 | Less than 20% |
| 0 | 0% |

Criteria the evaluation of phytotoxicity to paddy rice plant:

| Score | Inhibition of paddy rice plant as compared with the untreated control |
|---|---|
| 5 | 80% to 100% |
| 4 | Not less than 60% but less than 80% |
| 3 | Not less than 40% but less than 60% |
| 2 | Not less than 20% but less than 40% |
| 1 | Less than 20% |
| 0 | 0% |

TABLE 12

| Amount of test compound (g/10 a) | | Herbicidal effect | | | | | | Phytotoxicity to paddy rice plant |
|---|---|---|---|---|---|---|---|---|
| Compound (41) | Compound (a) | Barnyard grass | Monochoria | Toothcup | Umbrella plant | Hardstem bulrush | Cyperus serotinus | |
| 6.25 | 0 | 2 | 3 | 3 | 4 | 1 | 0 | 0 |
| 12.5 | 0 | 4 | 5 | 4.5 | 5 | 2 | 0 | 0 |
| 25 | 0 | 4.5 | 5 | 5 | 5 | 3 | 1 | 0 |
| 50 | 0 | 5 | 5 | 5 | 5 | 5 | 2 | 0 |
| 100 | 0 | 5 | 5 | 5 | 5 | 5 | 3 | 0 |
| 200 | 0 | 5 | 5 | 5 | 5 | 5 | 4 | 0 |
| 0 | 12.5 | 0 | 0.5 | 0.5 | 1 | 1 | 0 | 0 |
| 0 | 25 | 0 | 3 | 3 | 2.5 | 3.5 | 0.5 | 0 |
| 0 | 50 | 0.5 | 4.5 | 5 | 5 | 4 | 2 | 0 |
| 0 | 100 | 1 | 5 | 5 | 5 | 4.5 | 3 | 1 |
| 0 | 200 | 1 | 5 | 5 | 5 | 5 | 4.5 | 2 |
| 12.5 | 12.5 | 4 | 5 | 5 | 5 | 4 | 4.5 | 0 |
| 25 | 12.5 | 4.5 | 5 | 5 | 5 | 4 | 4 | 0 |
| 50 | 12.5 | 5 | 5 | 5 | 5 | 5 | 4.5 | 0 |
| 100 | 12.5 | 5 | 5 | 5 | 5 | 5 | 5 | 0 |
| 200 | 12.5 | 5 | 5 | 5 | 5 | 5 | 5 | 0 |
| 12.5 | 25 | 4.5 | 5 | 5 | 5 | 4.5 | 4.5 | 0 |
| 25 | 25 | 5 | 5 | 5 | 5 | 4.5 | 4.5 | 0 |
| 50 | 25 | 5 | 5 | 5 | 5 | 5 | 5 | 0 |
| 100 | 25 | 5 | 5 | 5 | 5 | 5 | 5 | 0 |
| 200 | 25 | 5 | 5 | 5 | 5 | 5 | 5 | 0 |
| 12.5 | 50 | 4.5 | 5 | 5 | 5 | 5 | 4.5 | 0 |
| 25 | 50 | 5 | 5 | 5 | 5 | 5 | 4.5 | 0 |
| 50 | 50 | 5 | 5 | 5 | 5 | 5 | 5 | 0 |
| 100 | 50 | 5 | 5 | 5 | 5 | 5 | 5 | 0 |
| 200 | 50 | 5 | 5 | 5 | 5 | 5 | 5 | 0 |
| 12.5 | 100 | 4.5 | 5 | 5 | 5 | 5 | 4.5 | 0 |
| 25 | 100 | 5 | 5 | 5 | 5 | 5 | 4.5 | 0 |
| 50 | 100 | 5 | 5 | 5 | 5 | 5 | 5 | 0 |
| 100 | 100 | 5 | 5 | 5 | 5 | 5 | 5 | 0 |
| 200 | 100 | 5 | 5 | 5 | 5 | 5 | 5 | 0 |
| No treatment | | 0 | 0 | 0 | 0 | 0 | 0 | 0 |

TABLE 13

(Herbicidal effect on arrowhead)

| Test compound and amount (g/10a) | | Compound (a) | | | | | |
|---|---|---|---|---|---|---|---|
| | | 0 | 12.5 | 25 | 50 | 100 | 200 |
| Compound (41) | 0 | 0 | 0 | 1 | 2 | 3.5 | 4.5 |
| | 6.25 | 0 | 0 | 1 | 2.5 | 4 | 5 |
| | 12.5 | 0 | 0 | 2.5 | 3.5 | 5 | 5 |
| | 25 | 0 | 1 | 3 | 4 | 5 | 5 |
| | 50 | 1 | 2 | 4.5 | 5 | 5 | 5 |
| | 100 | 2 | 4 | 4.5 | 5 | 5 | 5 |

TABLE 13-continued (Herbicidal effect on arrowhead)

| Test compound and amount (g/10a) | Compound (a) | | | | | |
|---|---|---|---|---|---|---|
| | 0 | 12.5 | 25 | 50 | 100 | 200 |

Utility Example 13

Submerged soil treatment

Paddy field soil was placed in a porcelain pot 12 cm in diameter and, after addition of water, plowed and sowed with barnyard grass (*Echinochloa crus-galli*), monochoria (*Monochoria vaginalis*), toothcup (*Rotala indica*), umbrella plant (*Cyperus difformis*) and hardstem bulrush (*Scirpus juncoides*). Furthermore, tubers of *Cyperus serotinus* were transplanted to the soil after forced sprouting. The two rice seedlings (*Oryza sativa* L., Nipponbare strain) at the two-leaf stage were transplanted in a bundle to the soil and the pot was filled with water to the height of 2 cm over the soil surface. One day after the transplantation of the rice seedlings, a wettable powder containing the test compound as prepared by the procedure of Formulation Example 2 was diluted with water to a prescribed concentration and the dilution was dropped onto the water surface. Eighteen days after the wettable powder treatment, the herbicidal effect and the phytotoxicity to the paddy rice plant (inhibition of growth of leaf sheath portion of the paddy rice plant) were evaluated according to the criteria described in Utility Example 12. The results obtained are shown in Table 14.

TABLE 14

| Test Compound | Amount of compound (g/10 a) | Herbicidal effect | | | | | | Phytotoxicity to paddy rice plant |
|---|---|---|---|---|---|---|---|---|
| | | Barnyard grass | Monochoria | Toothcup | Umbrella plant | Hardstem bulrush | *Cyperus serotinus* | |
| Compound (41) | 12.5 | 4 | 5 | 5 | 4.5 | 2 | 0 | 0 |
| | 25 | 4.5 | 5 | 5 | 5 | 3 | 1 | 0 |
| | 50 | 5 | 5 | 5 | 5 | 5 | 4 | 0 |
| Compound (b) | 25 | 0 | 1 | 2 | 0 | 1 | 0 | 0 |
| | 50 | 0 | 3 | 3 | 1 | 2 | 0 | 0 |
| | 100 | 1 | 4 | 4 | 4 | 4.5 | 1 | 1 |
| Compound (c) | 25 | 0 | 3 | 2 | 2 | 0 | 0 | 0 |
| | 50 | 0.5 | 4 | 3 | 5 | 2 | 1 | 0.5 |
| | 100 | 1 | 4.5 | 5 | 5 | 4 | 2 | 1.5 |
| Compound (41) + Compound (b) | 12.5 + 50 | 4 | 5 | 5 | 5 | 4.5 | 4.5 | 0 |
| | 25 + 50 | 4.5 | 5 | 5 | 5 | 5 | 5 | 0 |
| | 50 + 50 | 5 | 5 | 5 | 5 | 5 | 5 | 0 |
| Compound (41) + compound (c) | 12.5 + 50 | 4 | 5 | 5 | 5 | 5 | 4.5 | 0 |
| | 25 + 50 | 4.5 | 5 | 5 | 5 | 5 | 4.5 | 0 |
| | 50 + 50 | 5 | 5 | 5 | 5 | 5 | 5 | 0 |
| No treatment | | 0 | 0 | 0 | 0 | 0 | 0 | 0 |

Utility Example 14

Submerged soil treatment

Paddy field soil was placed in a porcelain pot 12 cm in diameter and, after addition of water, plowed, and sowed with barnyard grass (*Echinochloa crus-galli*), monochoria (*Monochoria vaginalis*), toothcup (*Rotala indica*), umbrella plant (*Cyperus difformis*) and hardstem bulrush (*Scirpus juncoides*). Furthermore, tubers of *Cyperus serotinus* were transplanted to the soil after forced sprouting. The pot was filled with water to the height of 2 cm over the soil surface. On the next day, a wettable powder containing the test compound as prepared by the procedure of Formulation Example 2 was diluted with water to a prescribed concentration and the dilution was dropped onto the water surface. The herbicidal effect was evaluated according to the criteria described in Utility Example 12 eighteen days after the wettable powder treatment. The results are shown in Table 15.

TABLE 15

| Test compound | Amount of compound (g/10 a) | Herbicidal effect | | | | | |
|---|---|---|---|---|---|---|---|
| | | Barnyard grass | Monochoria | Toothcup | Umbrella plant | Hardstem bulrush | *Cyperus serotinus* |
| Compound (32) | 25 | 4 | 4 | 5 | 5 | 1 | 1 |
| | 50 | 5 | 5 | 5 | 5 | 3 | 3.5 |
| | 100 | 5 | 5 | 5 | 5 | 4.5 | 5 |
| Compound (33) | 25 | 4 | 5 | 5 | 5 | 4 | 0 |
| | 50 | 4.5 | 5 | 5 | 5 | 4.5 | 1 |
| | 100 | 5 | 5 | 5 | 5 | 5 | 2 |
| Compound (39) | 25 | 4 | 5 | 4.5 | 4.5 | 3 | 0 |
| | 50 | 5 | 5 | 5 | 4.5 | 4.5 | 1 |
| | 100 | 5 | 5 | 5 | 4.5 | 5 | 2 |
| Compound (42) | 25 | 3 | 4 | 4 | 4 | 2 | 0 |
| | 50 | 3 | 4.5 | 4.5 | 4 | 3 | 1 |
| | 100 | 4 | 5 | 5 | 4.5 | 3.5 | 2 |
| Compound (43) | 25 | 4 | 5 | 5 | 5 | 1.5 | 0 |
| | 50 | 5 | 5 | 5 | 5 | 3.5 | 2 |
| | 100 | 5 | 5 | 5 | 5 | 4 | 2.5 |
| Compound (45) | 25 | 3.5 | 5 | 4.5 | 4.5 | 2 | 0 |
| | 50 | 5 | 5 | 5 | 5 | 4.5 | 1 |
| | 100 | 5 | 5 | 5 | 5 | 5 | 2 |
| Compound (a) | 25 | 0 | 3 | 4 | 2 | 2 | 0 |
| | 50 | 0 | 5 | 5 | 5 | 3 | 0 |
| | 100 | 2 | 5 | 5 | 5 | 5 | 1 |
| Compound (32) + compound (a) | 25 + 50 | 5 | 5 | 5 | 5 | 5 | 2 |
| | 50 + 50 | 5 | 5 | 5 | 5 | 5 | 4 |
| | 100 + 50 | 5 | 5 | 5 | 5 | 5 | 5 |
| Compound (33) + compound (a) | 25 + 50 | 4.5 | 5 | 5 | 5 | 5 | 3 |
| | 50 + 50 | 5 | 5 | 5 | 5 | 5 | 4 |
| | 100 + 50 | 5 | 5 | 5 | 5 | 5 | 5 |
| Compound (39) + compound (a) | 25 + 50 | 4.5 | 5 | 5 | 5 | 3.5 | 2 |
| | 50 + 50 | 5 | 5 | 5 | 5 | 5 | 3 |
| | 100 + 50 | 5 | 5 | 5 | 5 | 5 | 4 |
| Compound (42) + compound (a) | 25 + 50 | 3 | 4 | 4 | 4.5 | 3 | 2 |
| | 50 + 50 | 4 | 4.5 | 5 | 5 | 4.5 | 3.5 |
| | 100 + 50 | 5 | 5 | 5 | 5 | 5 | 4 |
| Compound (43) + compound (a) | 25 + 50 | 4 | 3 | 5 | 5 | 4 | 1 |
| | 50 + 50 | 5 | 4.5 | 5 | 5 | 5 | 3.5 |
| | 100 + 50 | 5 | 5 | 5 | 5 | 5 | 4 |
| Compound (45) + compound (a) | 25 + 50 | 5 | 3 | 5 | 5 | 4 | 1 |
| | 50 + 50 | 5 | 5 | 5 | 5 | 5 | 3 |
| | 100 + 50 | 5 | 5 | 5 | 5 | 5 | 4 |
| No treatment | | 0 | 0 | 0 | 0 | 0 | 0 |

Utility Example 15

Outdoor pot test (treatment with granular composition)

Sieved cultivated field soil was placed in a 1/5,000 are Wagner pot and, after addition of water, plowed and sowed with barnyard grass (*Echinochloa crus-galli*), monochoria (*Monochoria vaginalis*), toothcup (*Rotala indica*) and umbrella plant (*Cyperus difformis*). Furthermore tubers of *Cyperus serotinus* were transplanted to the soil after forced sprouting. Then two rice seedlings (*Oryza sativa* L., Nipponbare strain) at the two-leaf stage were transplanted in a bundle to the soil and the pot was filled with water to the height of 3 cm over the soil surface. Three days after the transplantation of the rice seedlings, a prescribed amount of a granular composition containing Compound (41) and Compound (a), which was prepared by the procedure of Formulation Example 8, was applied onto the water surface. The herbicidal effect on the weeds and injury to the paddy rice plant (inhibition of growth of the paddy rice plant) were evaluated 20 days after the application according to the criteria shown in Utility Example 12. The results obtained are shown in Table 16.

TABLE 16

| Amount of granular composition (kg/10a) | Herbicidal effect | | | | | Injury to the paddy rice plant |
|---|---|---|---|---|---|---|
| | Barnyard grass | Monochoria | Toothcup | Umbrella plant | *Cyperus serotinus* | |
| 1 | 5 | 5 | 5 | 5 | 4 | 0 |
| 2 | 5 | 5 | 5 | 5 | 4.5 | 0 |
| 3 | 5 | 5 | 5 | 5 | 4.5 | 0 |

Utility Example 16

Outdoor vat test (treatment with wettable powder)

Paddy field soil was placed in a 800 cm² vat and sowed with barnyard grass (*Echinochloa crus-galli*), monochoria (*Monochoria vaginalis*), toothcup (*Rotala indica*), umbrella plant (*Cyperus difformis*) and hardstem bulrush (*Scirpus juncoides*). Furthermore tubers of arrowhead (*Sagittaria pygmaea*) and *Cyperus serotinus* were embedded in the soil. The two rice seedlings (*Oryza sativa* L., Nipponbare strain) at the 2.5-leaf stage were transplanted in a bundle to the soil and the pot was filled with water to the height of 3 cm over the soil surface. A wettable powder containing Compound (32) and Compound (b), which was prepared by the procedure of Formulation Example 7, was diluted with water to a prescribed concentration and the resulting preparation was applied onto the water surface three days after the transplantation of the rice seedlings. The herbicidal effect on the weeds and injury to the paddy rice plant were evaluated 14 days after the application according to the criteria shown in Utility Example 12. The results obtained are shown in Table 17.

TABLE 17

| Amount of wettable powder (g/10a) | Herbicidal effect | | | | | | Injury to the paddy rice plant |
|---|---|---|---|---|---|---|---|
| | Barnyard grass | Tooth-cup | Umbrella plant | Hardstem bulrush | Arrow-head | *Cīperus serotinus* | |
| 200 | 5 | 5 | 5 | 5 | 3.5 | 4 | 0 |
| 400 | 5 | 5 | 5 | 5 | 4.5 | 4.5 | 0 |
| 800 | 5 | 5 | 5 | 5 | 5 | 4.5 | 0.5 |
| 1000 | 5 | 5 | 5 | 5 | 5 | 5 | 1 |

Utility Example 17

Test for phytotoxicity of a mixture of Compound (41) and Compound (a) to root of paddy rice plant Sieved paddy field soil was place in a porcelain pot 9 cm in diameter and, after addition of water, plowed. Thereto were transplanted two rice seedlings (*Oryza sative* L., Nipponbare strain) at the two-leaf stage in a bundle to the depth of 1 cm, and the pot was filled with water to the height of 2 cm over the soil surface. Three days after the transplantation of the rice seedlings, a wettable powder containing the test compound, which was prepared by the procedure of Formulation Example 2, was diluted with water to a prescribed concentration and the resulting preparation was applied onto the water surface. Nineteen days after the application, the root of the paddy rice plant was examined for phytotoxicity. The injury was evaluated according to the criteria shown in Utility Example 12. The results obtained are shown in Table 18.

TABLE 18

| Test compound and amount | | Compound (41) | | | | | |
|---|---|---|---|---|---|---|---|
| (g/10a) | | 0 | 12.5 | 25 | 50 | 100 | 200 |
| Compound (a) | 0 | 0 | 0 | 0 | 0 | 0 | 0 |
| | 50 | 1 | 0 | 0 | 0 | 0 | 0 |
| | 100 | 1.5 | 0.5 | 0 | 0 | 0 | 0 |
| | 200 | 3 | 1 | 0.5 | 0.5 | 0.5 | 0.5 |
| | 400 | 4 | 1.5 | 1 | 0.5 | 0.5 | 0.5 |

What is claimed is:
1. 4-chloro-3-propargyloxyphenyl 1-pyrrolidinecarboxylate.
2. 4,6-dichloro-3-propargyloxyphenyl 1-pyrrolidinecarboxylate.
3. 2,4-dichloro-5-propargyloxyphenyl 1-piperidinecarboxylate.
4. A method of controlling weeds which comprises applying to the area in which weeds are to be controlled an effective amount of 4-chloro-3-propargyloxyphenyl 1-pyrrolidinecarboxylate.
5. A method of controlling weeds which comprise applying to the area in which weeds are to be controlled an effective amount of 4,6-dichloro-3-propargyloxyphenyl 1-pyrrolidinecarboxylate.
6. A method of controlling weeds which comprises applying to the area in which weeds are to be controlled an effective amount of 2,4-dichloro-5-propargyloxyphenyl 1-piperidinecarboxylate.

7. A herbicidal composition which comprises (i) a herbicidally effective amount of 4-chloro-3-propargyloxyphenyl 1-piperidinecarboxylate, and (ii) a carrier therefor.

8. A herbicidal composition which comprises (i) a herbicidally effective amount of 4,6-dichloro-3-propargyloxyphenyl 1-pyrrolidinecarboxylate, and (ii) a carrier therefor.

9. A herbicidal composition which comprises (i) a herbicidally effective amount of 2,4-dichloro-5-propargyloxyphenyl 1-piperidinecarboxylate, and (ii) a carrier therefor.

* * * * *